(12) United States Patent
Klein et al.

(10) Patent No.: US 12,030,946 B2
(45) Date of Patent: Jul. 9, 2024

(54) THERAPEUTIC AND DIAGNOSTIC METHODS FOR CANCER

(71) Applicant: Hoffmann-La Roche Inc., Little Falls, NJ (US)

(72) Inventors: Christian Klein, Schlieren (CH); Laura Codarri Deak, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 327 days.

(21) Appl. No.: 16/270,334

(22) Filed: Feb. 7, 2019

(65) Prior Publication Data
US 2019/0315868 A1 Oct. 17, 2019

Related U.S. Application Data

(63) Continuation of application No. PCT/EP2017/069884, filed on Aug. 7, 2017.

(30) Foreign Application Priority Data

Aug. 8, 2016 (EP) .................................... 16183245
Jan. 4, 2017 (EP) .................................... 17150273

(51) Int. Cl.
C07K 16/28 (2006.01)
A61P 35/00 (2006.01)
C07K 14/705 (2006.01)

(52) U.S. Cl.
CPC .......... *C07K 16/2827* (2013.01); *A61P 35/00* (2018.01); *C07K 14/70532* (2013.01); *C07K 16/2818* (2013.01); *C07K 2317/21* (2013.01); *C07K 2317/24* (2013.01); *C07K 2317/56* (2013.01); *C07K 2317/76* (2013.01); *C07K 2319/30* (2013.01)

(58) Field of Classification Search
CPC .......... C07K 16/2827; C07K 14/70532; C07K 16/2818; C07K 2317/21; C07K 2317/24; C07K 2317/56; C07K 2317/76; C07K 2319/30; A61P 35/00; A61P 43/00; A61P 35/04; A61P 13/10
See application file for complete search history.

(56) References Cited

U.S. PATENT DOCUMENTS

| 8,217,149 | B2 | 7/2012 | Irving et al. | |
| 2010/0203056 | A1* | 8/2010 | Irving et al. | A61K 39/395 |
| 2013/0034559 | A1 | 2/2013 | Queva et al. | |
| 2019/0269666 | A1* | 9/2019 | Schaer et al. | A61K 31/4439 |

FOREIGN PATENT DOCUMENTS

| WO | 2006/121168 A1 | 11/2006 |
| WO | 2007/005874 A2 | 1/2007 |
| WO | 2009/114335 A2 | 9/2009 |
| WO | 2010/027827 A2 | 3/2010 |
| WO | 2010/027827 A3 | 3/2010 |
| WO | 2010/077634 A1 | 7/2010 |
| WO | 2011/066342 A2 | 6/2011 |
| WO | 2011/066389 A1 | 6/2011 |
| WO | 2016/022630 A1 | 2/2016 |
| WO | 2016/109546 A2 | 7/2016 |

OTHER PUBLICATIONS

Lindqvist CA, Christiansson LH, Thörn I, et al. Both CD4+ FoxP3+ and CD4+ FoxP3-T cells from patients with B-cell malignancy express cytolytic markers and kill autologous leukemic B cells in vitro. Immunology. 2011;133(3):296-306. doi:10.1111/j.1365-2567.2011.03439.x (Year: 2011).*
Kelley TW, Pohlman B, Elson P, Hsi ED. The ratio of FOXP3+ regulatory T cells to granzyme B+ cytotoxic T/NK cells predicts prognosis in classical Hodgkin lymphoma and is independent of bcl-2 and MAL expression. Am J Clin Pathol. 2007;128(6):958-965. doi:10.1309/NB3947K383DJOLQ2 (Year: 2007).*
Li Y, Li F, Jiang F, et al. A Mini-Review for Cancer Immunotherapy: Molecular Understanding of PD-1/PD-L1 Pathway & Translational Blockade of Immune Checkpoints. Int J Mol Sci. 2016; 17(7):1151. Published Jul. 18, 2016. doi:10.3390/ijms17071151 (Year: 2016).*
Lin, L., Couturier, J., Yu, X. et al. Granzyme B secretion by human memory CD4 T cells is less strictly regulated compared to memory CD8 T cells. BMC Immunol 15, 36 (2014). https://doi.org/10.1186/s12865-014-0036-1 (Year: 2014).*
Duraiswamy J, Freeman GJ, Coukos G. Therapeutic PD-1 pathway blockade augments with other modalities of immunotherapy T-cell function to prevent immune decline in ovarian cancer. Cancer Res. Dec. 1, 2013;73(23):6900-12. (Year: 2013).*
Wang et al., "PD1 blockade reverses the suppression of melanoma antigen-specific CTL by CD4+CD25Hi regulatory T cells" International Immunology 21(9):1065-1077 (Jul. 2009).
Azuma, "Immune Checkpoint Inhibitor—Saizensen-" Farumacia 53(1) ( 2017).
Nomi et al., "Clinical significance and therapeutic potential of the programmed death-1 ligand/programmed death-1 pathway in human pancreatic cancer" Clin Cancer Res 13(7):2151-7 (Apr. 2007).
Sunshine et al., "PD-1/PD-L1 inhibitors" Current Opinion in Pharmacology 23:32-38 ( 2015).

(Continued)

*Primary Examiner* — Hong Sang
*Assistant Examiner* — Francesca Edgingtongiordan
(74) *Attorney, Agent, or Firm* — Susan T. Hubl

(57) ABSTRACT

The present invention provides therapeutic and diagnostic methods and compositions for cancer and for enhancing immune function in an individual having cancer. The invention provides methods of treatment, methods for determining whether an individual suffering from a cancer is responding to treatment comprising a PD-1 axis binding antagonist, predicting responsiveness of an individual suffering from a cancer to treatment comprising a PD-1 axis binding antagonist, and methods of selecting a therapy for an individual suffering from cancer.

6 Claims, 13 Drawing Sheets
(2 of 13 Drawing Sheet(s) Filed in Color)
Specification includes a Sequence Listing.

(56) References Cited

OTHER PUBLICATIONS

Zhi et al., "Advances in Research on Cancer Immunotherapy Targeting T Cell Co-signalling" Progress in Pharmaceutical Sciences 39(9):659-665 (Sep. 2015).
Anegawa et al., "Upregulation of granzyme B and interferon-γ mRNA in responding lesions by treatment with nivolumab for metastatic melanoma: a case report" Journal of the European Academy of Dermatology and Venereology 30(8):e231-e232 ( 2015).
Ansell et al., "PD-1 Blockade with Nivolumab in Relapsed or Refractory Hodgkin's Lymphoma" The New England Journal of Medicine 372(4):311-319 ( 2015).
Appay et al., "The physiological role of cytotoxic CD4(+) T-cells: the holy grail?" Clinical and Experimental Immunology 138:10-13 ( 2004).
CAS Registry Database, 946414-94-4, Sep. 7, 2007.
International Preliminary Report on Patentability (IPRP) for PCT/EP2017/069884 issued on Feb. 12, 2019.
International Search Report for PCT/EP2017/069884 mailed on Dec. 19, 2017.
Kelley et al., "The Ratio of FOXP3+ Regulatory T Cells to Granzyme B+ Cytotoxic T/NK Cells Predicts Prognosis in Classical Hodgkin Lymphoma and Is Independent of bcl-2 and MAL Expression" American Journal of Clinical Pathology 128(6):958-965 ( 2007).
Kreiter et al., "Mutant MHC class II epitopes drive therapeutic immune responses to cancer" Nature 520:692-696 ( 2015).
Linnemann et al., "High-throughput epitope discovery reveals frequent recognition of neo-antigens by CD4+ T cells in human melanoma" Nature Medicine 21:81-85 ( 2015).
Llosa et al., "The Vigorous Immune Microenvironment of Microsatellite Instable Colon Cancer Is Balanced by Multiple Counter-Inhibitory Checkpoints" Cancer Discovery 5:43-51 ( 2015).
Quezada et al., "Tumor-reactive CD4+ T cells develop cytotoxic activity and eradicate large established melanoma after transfer into lymphopenic hosts" J. Exp. Med. 207:637-650 ( 2010).

* cited by examiner

THERAPEUTIC AND DIAGNOSTIC METHODS FOR CANCER

CROSS REFERENCE TO RELATED APPLICATIONS

This application is a continuation of International Application No. PCT/EP2017/069884 having an International Filing Date of Aug. 7, 2017, the entire contents of which are incorporated herein by reference, and which claims the benefit of priority under 35 U.S.C. § 119 to EP 17150273.5 filed Jan. 4, 2017 and EP 16183245.6 filed on Aug. 8, 2016.

SEQUENCE LISTING

The instant application contains a Sequence Listing submitted electronically in ASCII format and is hereby incorporated herein by reference in its entirety. Said ASCII copy, created Jan. 29, 2019, is named P33752-US_sequence_listing.txt and is 32,768 bytes in size.

FIELD OF THE INVENTION

Provided herein are therapeutic and diagnostic methods and compositions for pathological conditions, such as cancer (e.g., melanoma), and methods of using PD-1 axis binding antagonists. In particular, the invention provides methods of monitoring response to treatment, methods of treatment, articles of manufacture and kits.

BACKGROUND OF THE INVENTION

Cancer remains one of the most deadly threats to human health. Cancers, or malignant tumors, metastasize and grow rapidly in an uncontrolled manner, making timely detection and treatment extremely difficult.

Programmed death 1 polypeptide (PD-1), which binds to ligands that include PD-L1 and PD-L2. Programmed death-ligand 1 (PD-L1) has been implicated in the suppression of immune system responses during chronic infections, pregnancy, tissue allografts, autoimmune diseases, and cancer. The majority of tumor-infiltrating T lymphocytes predominantly express PD-1, in contrast to T lymphocytes in normal tissues and the peripheral blood. Formation of the PD-L1/PD-1 and PD-L1/B7-1 complexes is thought to negatively regulate T-cell receptor signaling, resulting in the subsequent downregulation of CD8+ T-cell activation and CD8+ T-cell-mediated tumor cell killing.

Studies focusing on the CD8+ T-cell compartment within the tumor microenvironment failed so far to reveal the mechanism of action of anti-PD-1 immunotherapy despite a clear clinical benefit in a substantial portion, roughly 30%, of treated patients. While studies have largely focused on CD8+ T cells, it was recently observed that tumor infiltrating $CD4^+$ T cells in micro-satellite instable tumors express higher levels of PD-1 than those in micro-satellite stable tumors (Llosa and Cruise, Cancer discovery 5(1): 43-51 (2015)). In addition in melanoma, tumor infiltrating $CD4^+$ T cells frequently recognize the mutated antigens (Linnemann and van Buuren, Nature medicine 21(1): 81-85 (2015)). In line with these studies, experiments performed in animal models of colorectal cancer and melanoma, demonstrated that MHC class II-restricted T cell responses can play an important role in tumor control (Kreiter et al., Nature 520(7549): 692-696 (2015)) and that tumor-reactive $CD4^+$ T cells can develop cytotoxic abilities and eradicate large established tumors (Quezada et al., J Exp. Med., 207(3): 637-650 (2010)). Prior to the studies reported herein, it was not known if and how PD-1 blocking agents, e.g., anti-PD-1 antibodies, affect $CD4^+$ T cells in a human cancer context.

There remains a need to monitor and optimize treatment strategies that includes blockade of PD-1 receptor/ligand interaction for treating, stabilizing, preventing, and/or delaying development of various cancers, e.g., melanoma. Specifically, there remains a need for identifying patients likely to respond to such treatment and methods for rapidly monitoring effectiveness of ongoing treatment.

SUMMARY OF THE INVENTION

This invention relates to therapeutic and diagnostic methods and compositions for cancer. In one aspect, the invention features a method for treating or delaying progression of a cancer in an individual comprising administering to the patient a therapeutically effective amount of a PD-1 axis binding antagonist, wherein the ratio between Granzyme B+$CD4^+$ T cells and FOXP3$^+$ $CD4^+$ T cells in a blood sample obtained from the patient has been determined to be 1 or greater.

In one aspect, the invention relates to methods for determine whether an individual suffering from a cancer is responding to treatment comprising a PD-1 axis binding antagonist, the method comprising determining the ratio between Granzyme B+$CD4^+$ T cells and FOXP3$^+$ $CD4^+$ T cells in a sample obtained from the individual, wherein a ratio between Granzyme B$^+$ $CD4^+$ T cells and FOXP3$^+$ $CD4^+$ T cells of 1 or greater in the sample indicates that the individual is responding to treatment comprising a PD-1 axis binding antagonist.

In some embodiments of the above aspects, the sample is a blood sample. In some embodiments, the sample is a whole blood sample or a peripheral blood mononuclear cell sample. In some embodiments, the blood sample has been collected from the individual no later than 2 months following the last treatment with the PD-1 antagonist. In some embodiments, the individual is receiving or has received treatment comprising a PD-1 axis binding antagonist. In some embodiments, the cancer is selected from the group consisting of bladder cancer, squamous cell cancer, lung cancer including small-cell lung cancer (SCLC), non-small cell lung cancer (NSCLC), adenocarcinoma of the lung, squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, hepatoma, breast cancer, colon cancer, rectal cancer, colorectal cancer, endometrial or uterine carcinoma, salivary gland carcinoma, renal cancer, prostate cancer, vulval cancer, thyroid cancer, hepatic carcinoma, anal carcinoma, penile carcinoma, Merkel cell cancer, testicular cancer, esophageal cancer, tumors of the biliary tract, head and neck cancer and hematological malignancies. In some embodiments, the cancer is melanoma.

In some embodiments, the cancer is an urothelial bladder cancer. In some embodiments, the urothelial bladder cancer is a metastatic urothelial bladder cancer. In some embodiments, the urothelial bladder cancer is a locally advanced urothelial bladder cancer. In some embodiments, the cancer cells in the individual express PD-L1.

In some embodiments, PD-L1 expression is determined by an immunohistochemistry (IHC) assay. In some embodiments, the individual has received two or fewer prior cytotoxic treatment regimens for locally advanced or metastatic cancer (e.g., 0, 1, or 2 prior cytotoxic treatment regimen(s)).

In some embodiments, the individual has never had prior targeted systemic treatment for locally advanced or metastatic cancer. In some embodiments, the response of the individual to the treatment is a complete response. In some embodiments, the response of the individual to the treatment is a partial response. In some embodiments, the response of the individual to the treatment is a sustained response after cessation of the treatment.

In some embodiments, the ratio between Granzyme B$^+$ CD4$^+$ T cells and FOXP3$^+$ CD4$^+$ T cells is 4. In some embodiments, the ratio between Granzyme B$^+$ CD4$^+$ T cells and FOXP3$^+$ CD4$^+$ T cells is 45.

In some embodiments of the above aspects, the PD-L1 axis binding antagonist is selected from a PD-L1 binding antagonist, a PD-1 binding antagonist, and a PD-L2 binding antagonist. In some embodiments, the PD-L1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an antibody. In some embodiments, the antibody is selected from the group consisting of atezolizumab (MPDL3280A), YW243.55.S70, MDX-1105, MED14736 (durvalumab), and MSB0010718C (avelumab). In some embodiments, the antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24. In some embodiments, the antibody comprises a heavy chain variable region comprising the amino acid sequence of SEQ ID NO:25 and a light chain variable region comprising the amino acid sequence of SEQ ID NO:4.

In some embodiments, the PD-L1 axis binding antagonist is a PD-1 binding antagonist. In some embodiments, the PD-1 binding antagonist inhibits the binding of PD-1 to one or more of its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an antibody. In some embodiments, the antibody is selected from the group consisting of: MDX-1106 (nivolumab), MK-3475 (pembrolizumab), MEDI-0680 (AMP-514), PDR001, REGN2810, and BGB-108.

In some embodiments, the PD-1 binding antagonist is an Fc-fusion protein. In some embodiments, the Fc-fusion protein is AMP-224.

In any of the preceding embodiments of the above aspects, the individual is receiving or has received an effective amount of a second therapeutic agent. In some embodiments, the second therapeutic agent is selected from the group consisting of a cytotoxic agent, a growth-inhibitory agent, a radiation therapy agent, an anti-angiogenic agent, and combinations thereof. In some embodiments, the cytotoxic agent is a chemotherapeutic agent. In some embodiments, the chemotherapeutic agent is a taxane. In some embodiments, the taxane is administered before the PD-1 axis binding antagonist, simultaneous with the PD-1 axis binding antagonist, or after the PD-1 axis binding antagonist. In some embodiments, the taxane is nab-paclitaxel (ABRAXANE®), paclitaxel, or docetaxel. In some embodiments, the individual has progressed following treatment with a platinum-based chemotherapeutic agent.

In any of the preceding embodiments of the above aspects, the ratio between Granzyme B$^+$ CD4$^+$ T cells and FOXP3$^+$ CD4$^+$ T cells is determined by determining the number of CD4$^+$ T cells expressing Granzyme B protein and the number of CD4$^+$ T cells expressing FOXP3 protein. In some embodiments, the protein expression level of at least one of Granzyme B and FOXP3 is determined using a method selected from the group consisting of immunohistochemistry (IHC), immunofluorescence, flow cytometry, and Western blot. In some embodiments, the protein expression level of at least one of Granzyme B and FOXP3 is determined using flow cytometry. In some embodiments, the expression level of at least one of Granzyme B and FOXP3 is an mRNA expression level. In some embodiments, the mRNA expression level of at least one of Granzyme B and FOXP3 is determined using a method selected from the group consisting of quantitative polymerase chain reaction (qPCR), reverse transcription qPCR (RT-qPCR), RNA sequencing, microarray analysis, in situ hybridization, and serial analysis of gene expression (SAGE).

In another aspect, the invention features a method for predicting responsiveness of an individual suffering from a cancer to treatment comprising a PD-L1 axis binding antagonist, the method comprising determining the the ratio between Granzyme B$^+$ CD4$^+$ T cells and FOXP3$^+$ CD4$^+$ T cells in a sample obtained from the individual, wherein a ratio between Granzyme B$^+$ CD4$^+$ T cells and FOXP3$^+$ CD4$^+$ T cells of 1 or greater indicates that the individual is likely to respond to treatment comprising a PD-1 axis binding antagonist. In some embodiments, the sample if obtained from the individual after the individual has received at least one dose of a PD-L1 axis binding antagonist.

In another aspect, the invention features a method for selecting a therapy for an individual suffering from a cancer, the method comprising determining the the ratio between Granzyme B$^+$ CD4$^+$ T cells and FOXP3$^+$ CD4$^+$ T cells in a sample obtained from the individual, and selecting a therapy comprising a PD-L1 axis binding antagonist for the individual based on a ratio between Granzyme B$^+$ CD4$^+$ T cells and FOXP3$^+$ CD4$^+$ T cells of 1 or greater in the sample.

In another aspect, the invention features a PD-L1 axis binding antagonist for use in treating an individual suffering from a cancer, wherein the ratio between Granzyme B$^+$ CD4$^+$ T cells and FOXP3$^+$ CD4$^+$ T cells in a blood sample obtained from the individual has been determined to be 1 or greater.

In another aspect, the invention features use of an effective amount of a PD-1 axis binding antagonist in the manufacture of a medicament for use in treating an individual suffering from a cancer, wherein the ratio between Granzyme B$^+$ CD4$^+$ T cells and FOXP3$^+$ CD4$^+$ T cells in a blood sample obtained from the individual has been determined to be 1 or greater.

In another aspect, the invention features a composition comprising an effective amount of a PD-1 axis binding antagonist for use in a method of treating an individual suffering from a cancer, wherein the ratio between Granzyme B$^+$ CD4$^+$ T cells and FOXP3$^+$ CD4$^+$ T cells in a blood sample obtained from the individual has been determined to be 1 or greater.

In another aspect, the invention features a method of enhancing immune function in an individual having melanoma with a PD-1 axis binding antagonist comprising: administering to the individual an effective amount of the PD-1 axis binding antagonist, wherein the ratio between Granzyme B$^+$ CD4$^+$ T cells and FOXP3$^+$ CD4$^+$ T cells in a blood sample obtained from the individual has been determined to be 1 or greater. In one embodiment, the number of Granzyme B$^+$ CD4$^+$ T cells in a blood sample obtained from the individual is elevated relative to prior to administration of the PD-1 axis binding antagonist. In one embodiment, the number of FOXP3$^+$ CD4$^+$ T cells in a blood sample obtained from the individual is reduced relative to prior to the administration of the PD-1 axis binding antagonist. In one embodiment, T cell exhaustion is decreased relative to prior to the administration of the PD-1 axis binding antagonist.

In another aspect, the invention features a method of selecting an individual for treatment and treating or delaying progression of a cancer in an individual, the method comprising (a) obtaining a blood sample from the individual; (b) determining the ratio between Granzyme B$^+$ CD4$^+$ T cells and FOXP3$^+$ CD4$^+$ T cells in a blood sample obtained from the individual; (c) selecting the individual for treatment comprising a PD-1 axis binding antagonist if the ratio between Granzyme B$^+$ CD4$^+$ T cells and FOXP3$^+$ CD4$^+$ T cells is 1 or greater; and (d) administering the PD-1 axis binding antagonist to the individual.

In another aspect, the invention features a kit comprising a medicament comprising a PD-1 axis binding antagonist and an optional pharmaceutically acceptable carrier, and a package insert comprising instructions for administration of the medicament for treating or delaying progression of a cancer in an individual, wherein the ratio between Granzyme B$^+$ CD4$^+$ T cells and FOXP3$^+$ CD4$^+$ T cells in a blood sample obtained from the individual has been determined to be 1 or greater. In some embodiments, the PD-1 axis binding antagonist is a PD-L1 binding antagonist. In some embodiments, the PD-L1 binding antagonist is MPDL3280A. In some embodiments, the medicament comprises MPDL3280A at a dose of about 840 mg. In some embodiments, the package insert comprises instructions for administration of the medicament once every two weeks to the individual.

In any one of the preceding aspects, the PD-1 axis binding antagonist may be selected from the group consisting of a PD-1 binding antagonist, a PD-L1 binding antagonist, and a PD-L2 binding antagonist. In some embodiments, the PD-1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an antibody. In some embodiments, the PD-1 binding antagonist is selected from the group consisting of MDX 1106 (nivolumab), MK-3475 (pembrolizumab), MEDI-0680 (AMP-514), PDR001, REGN2810, and BGB-108. In some embodiments, the PD-1 axis binding antagonist is a PD-L1 binding antagonist. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an antibody. In some embodiments, the antibody is selected from the group consisting of: MPDL3280A (atezolizumab), YW243.55.S70, MDX-1105, MED14736 (durvalumab), and MSB0010718C (avelumab). In some embodiments, the antibody comprises a heavy chain comprising an HVR-H1 sequence of SEQ ID NO:19, HVR-H2 sequence of SEQ ID NO:20, and HVR-H3 sequence of SEQ ID NO:21; and a light chain comprising an HVR-L1 sequence of SEQ ID NO:22, HVR-L2 sequence of SEQ ID NO:23, and HVR-L3 sequence of SEQ ID NO:24. In some embodiments, the antibody comprises a heavy chain variable region comprising the amino acid sequence of SEQ ID NO:26 and a light chain variable region comprising the amino acid sequence of SEQ ID NO:4. In some embodiments, the antibody comprises a heavy chain variable region comprising the amino acid sequence of SEQ ID NO:25 and a light chain variable region comprising the amino acid sequence of SEQ ID NO:4.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

The application file contains at least one drawing executed in color. Copies of this patent or patent application with color drawings will be provided by the Office upon request and payment of the necessary fee.

FIGS. 3A and B show representative FACS plots, gated on CD4, depicting the frequencies of Granzyme B positive CFSE low CD4 T cells in mMLR assay alone (FIG. 3A) or after five days of PD-1 blockade (FIG. 3B). The y axis: Granyame B; x axis: CFSE. FIG. 3C shows a graph summarizing the frequencies of CD4 T cells producing Granzyme B upon 5 days co-culture with allo-DCs with or without anti-PD-1 blocking antibody or with an isotype control antibody. Each data point (circle, square or triangle) represents one donor from each independent experiment.

FIGS. 6A and B show the frequencies of regulatory T cells (FOXP3) versus Granzyme B$^+$ within CD4$^+$ T cells from the same melanoma patient at two different time points: FIG. 6A shows results while the patient is responding to the anti-PD-1 (MDX-1106) therapy and FIG. 6B shows results for the same patient 4 months later during a relapse.

DETAILED DESCRIPTION OF EMBODIMENTS OF THE INVENTION

I. Definitions

Figure 1A:
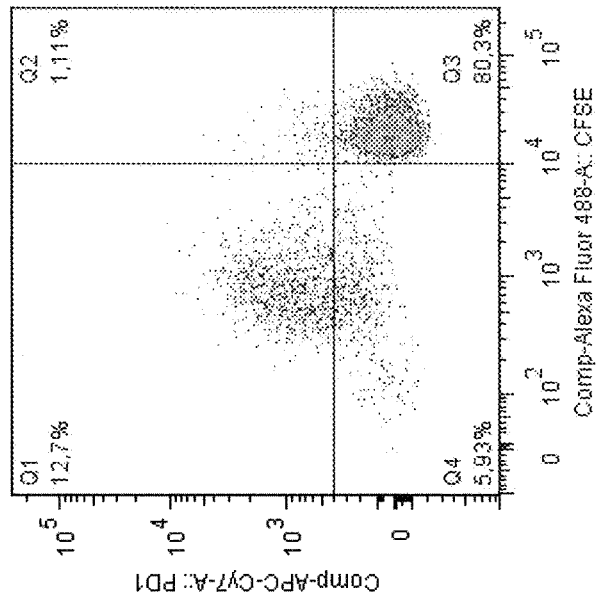
FIGS. 1A and B show PD-1 expression in CD4$^+$ T cells alone (FIG. 1A) and in CD4$^+$ T cells with allogeneic DCs in a mMLR assay (FIG. 1B). The y axis indicates PD-1 expression and the x axis indicates CFSE expression.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, and/or target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen-binding fragments thereof, immunoadhesins, fusion proteins, oligopeptides, and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (pembrolizumab) described herein. In another specific aspect, a PD-1 binding antagonist is MEDI-0680 (AMP-514) described herein. In another specific aspect, a PD-1 binding antagonist is PDR001 described herein. In another specific aspect, a PD-1 binding antagonist is REGN2810 described herein. In another specific aspect, a PD-1 binding antagonist is BGB-108 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1 and/or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen-binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 and/or B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is MPDL3280A (atezolizumab) described herein. In another specific aspect, an anti-PD-L1 antibody is MDX-1105 described herein. In still another specific aspect, an anti-PD-L1 antibody is YW243.55.S70 described herein. In still another specific aspect, an anti-PD-L1 antibody is MED14736 (durvalumab) described herein. In still another specific aspect, an anti-PD-L1 antibody is MSB0010718C (avelumab) described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

A "taxane" as used herein is a diterpene which may bind to tubulin, promoting microtubule assembly and stabilization and/or prevent microtubule depolymerization. Taxanes included herein include taxoid 10-deacetylbaccatin III and/or derivatives thereof. Examplary taxanes include, but are not limited to, paclitaxel (i.e., TAXOL®, CAS #33069-62-4), docetaxel (i.e., TAXOTERE®, CAS #114977-28-5), larotaxel, cabazitaxel, milataxel, tesetaxel, and/or orataxel. In some embodiments, the taxane is an albumin-coated nanoparticle (e.g., nano-albumin bound (nab)-paclitaxel, i.e., ABRAXANE® and/or nab-docetaxel, ABI-008). In some embodiments, the taxane is nab-paclitaxel (ABRAXANE®). In some embodiments, the taxane is formulated in CREMAPHOR® (e.g., TAXOL®) and/or in Tween such as polysorbate 80 (e.g., TAXOTERE®). In some embodiments, the taxane is liposome-encapsulated taxane. In some embodiments, the taxane is a prodrug form and/or conjugated form of taxane (e.g., DHA covalently conjugated to paclitaxel, paclitaxel poliglumex, and/or linoleyl carbonate-paclitaxel). In some embodiments, the paclitaxel is formulated with substantially no surfactant (e.g., in the absence of CREMAPHOR and/or Tween-such as TOCOSOL® paclitaxel).

The term "dysfunction" in the context of immune dysfunction, refers to a state of reduced immune responsiveness to antigenic stimulation. The term includes the common elements of both "exhaustion" and/or "anergy" in which antigen recognition may occur, but the ensuing immune response is ineffective to control infection or tumor growth.

The term "dysfunctional," as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

As used herein, "cytotoxic CD4$^+$ T cell" refers to a cytotoxic Granzyme B$^+$ CD4$^+$ T cell. The terms "cytotoxic CD4$^+$ T cells," "CD4$^+$ cytotoxic T cells," and "cytotoxic Granzyme B$^+$ CD4$^+$ T cells" are used synonomously. These cells can be identified by methods known in the art, e.g., by staining cells with fluorescently labeled antibodies to CD4 and to Granzyme B and using fluorescence activated cell sorting, gating on CD4-positive cells and Granzyme B double-positive cells.

As used herein, regulatory T cells or Tregs refer to FOXP3$^+$ CD4$^+$ T cells. The terms "regulatory T cell," "Tregs," and "FOXP3$^+$ CD4$^+$ T cells" are used synonomously. These cells can be identified by methods known in the art, e.g., by staining cells with fluorescently labeled antibodies to CD4 and to FOXP3 and using fluorescence activated cell sorting, gating on CD4-positive cells and FOXP3 double-positive cells.

As used herein, "ratio between Granzyme B$^+$ CD4$^+$ T cells and FOXP3$^+$ CD4$^+$ T cells" refers to the frequency of Granzyme B$^+$ CD4$^+$ T cells divided by FOX3P CD4$^+$ T cells within a CD4-positive cell population.

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from CD8+ T-cells, increased proliferation, increased antigen responsiveness (e.g., viral, pathogen, or tumor clearance) relative to such levels before the intervention. In one embodiment, the level of enhancement is at least 50%, alternatively 60%, 70%, 80%, 90%, 100%, 120%, 150%, or 200% enhancement. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include treatment with a PD-1 axis binding antagonist and a taxane.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

As used herein, "complete response" or "CR" refers to disappearance of all target lesions.

As used herein, "partial response" or "PR" refers to at least a 30% decrease in the sum of the longest diameters (SLD) of target lesions, taking as reference the baseline SLD.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" or "objective response rate" (ORR) refers to the sum of complete response (CR) rate and partial response (PR) rate.

As used herein, "overall survival" (OS) refers to the percentage of individuals in a group who are likely to be alive after a particular duration of time.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals.

As used herein, "delaying progression" of a disease means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" or "therapeutically effective amount" is at least the minimum amount required to effect a measurable improvement or prevention of a particular disorder. An effective amount herein may vary according to factors such as the disease state, age, sex, and weight of the patient, and the ability of the agent to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, and enhancing effect of another medication such as via targeting, delaying the progression of the disease, and/or prolonging survival.

In the case of a cancer or a tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

The term "tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, 1, or 2 cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include bladder cancer (e.g., urothelial bladder cancer (e.g., transitional cell or urothelial carcinoma, non-muscle invasive bladder cancer, muscle-invasive bladder cancer, and metastatic bladder cancer) and non-urothelial bladder cancer), squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, as well as head and neck cancer and hematological malignancies. In some embodiments, the cancer is triple-negative metastatic breast cancer, including any histologically confirmed triple-negative (ER-, PR-, HER2-) adenocarcinoma of the breast with locally recurrent or metastatic disease (where the locally recurrent disease is not amenable to resection with curative intent). In some embodiments, the cancer is bladder cancer. In particular embodiments, the bladder cancer is urothelial bladder cancer.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. For instance, a "tumor sample" is a tissue sample obtained from a tumor or other cancerous tissue. The tissue sample may contain a mixed population of cell types (e.g., tumor cells and non-tumor cells, cancerous cells and non-cancerous cells). The tissue sample may contain compounds which are not naturally intermixed with the tissue in nature such as preservatives, anticoagulants, buffers, fixatives, nutrients, antibiotics, or the like.

The term "detection" includes any means of detecting, including direct and indirect detection.

The term "biomarker" as used herein refers to an indicator, e.g., predictive, diagnostic, and/or prognostic, which can be detected in a sample. The biomarker may serve as an indicator of a particular subtype of a disease or disorder (e.g., cancer) characterized by certain, molecular, pathological, histological, and/or clinical features. In some embodiments, a biomarker is a gene.

Biomarkers include, but are not limited to, polynucleotides (e.g., DNA and/or RNA), polynucleotide copy number alterations (e.g., DNA copy numbers), polypeptides, polypeptide and polynucleotide modifications (e.g., posttranslational modifications), carbohydrates, and/or glycolipid-based molecular markers.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signalling inhibitors, HDAC inhibitors, proteasome inhibitors, and inhibitors of cancer metabolism. In one embodiment the cytotoxic agent is a platinum-based chemotherapeutic agent. In one embodiment the cytotoxic agent is an antagonist of EGFR. In one embodiment the cytotoxic agent is N-(3-ethynylphenyl)-6,7-bis(2-methoxyethoxy)quinazolin-4-amine (e.g., erlotinib, TARCEVA™). In one embodiment the cytotoxic agent is a RAF inhibitor. In one embodiment, the RAF inhibitor is a BRAF and/or CRAF inhibitor. In one embodiment the RAF inhibitor is vemurafenib. In one embodiment the cytotoxic agent is a PI3K inhibitor.

As used herein, the term "chemotherapeutic agent" includes compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, rapamycin (Sirolimus, RAPAMUNE®, Wyeth), Lapatinib (TYKERB®, GSK572016, Glaxo Smith Kline), lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1| and calicheamicin ω1| (*Angew Chem. Intl. Ed. Engl.* 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxanes; chloranmbucil; GEMZAR® (gemcitabine); 6-thioguanine; mercaptopurine; methotrexate; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agents also include "platinum-based" chemotherapeutic agents, which comprise an organic compound which contains platinum as an integral part of the molecule. Typically platinum-based chemotherapeutic agents are coordination complexes of platinum. Platinum-based chemotherapeutic agents are sometimes called "platins" in the art. Examples of platinum-based chemotherapeutic agents include, but are not limited to, carboplatin, cisplatin, and oxaliplatin.

Chemotherapeutic agents also include (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agents also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$λ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533) and variants thereof, such as chimerized 225 (C225 or Cetuximab; ERBUTIX®) and reshaped human 225 (H225) (see, e.g., WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al., *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl) amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl) amino]-1H-pyrrolo[2,3-d]pyrimidin-6-yl]-phenol); (R)-6-(4-hydroxyphenyl)-4-[(1-phenylethyl)amino]-7H-pyrrolo [2,3-d]pyrimidine); CL-387785 (N-[4-[(3-bromophenyl) amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl) methoxy]phenyl]-6[5[[[2methylsulfonyl)ethyl]amino] methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER-targeted tyrosine kinase inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g., celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

A "growth inhibitory agent" when used herein refers to a compound or composition which inhibits growth of a cell either in vitro or in vivo. In one embodiment, a growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

An "individual" or a "subject" for purposes of treatment refers to any animal classified as a mammal, including humans, domestic and farm animals, and zoo, sports, or pet animals, such as dogs, horses, cats, cows, etc. An individual or subject may be a patient. In particular embodiments, the individual or patient is a human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively.

The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen-binding region thereof. In some embodiments, the antibody fragment described herein is an antigen-binding fragment. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg et al., *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng*, 8(10):1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

As used herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

II. PD-1 Axis Binding Antagonists

Provided herein are methods of treating a patient suffering from a cancer, the method comprising administering to the patient a therapeutically effective amount of a PD-1 axis binding antagonist, wherein the ratio between Granzyme $B^+$ $CD4^+$ T cells and $FOXP3^+$ $CD4^+$ T cells in a blood sample obtained from the patient has been determined to be 1 or greater. Also provided herein are methods for determining whether a patient suffering from a cancer is likely to respond to treatment comprising a PD-1 axis binding antagonist. For example, a PD-1 axis binding antagonist includes a PD-1 binding antagonist, a PD-L1 binding antagonist and a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1LG2," "CD273," "B7-DC," "Btdc," and "PDL2." An exemplary human PD-L2 is shown in UniProtKB/Swiss-Prot Accession No. Q9BQ51. In some embodiments, PD-1, PD-L1, and PD-L2 are human PD-1, PD-L1 and PD-L2.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of MDX 1106 (nivolumab), MK-3475 (pembrolizumab), MEDI-0680 (AMP-514), PDR001, REGN2810, and BGB-108. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 antibody is selected from the group consisting of MPDL3280A, YW243.55.S70, MDX-1105, MED14736 (durvalumab), and MSB0010718C (avelumab). Antibody YW243.55.S70 is an anti-PD-L1 described in WO 2010/077634. MDX-1105, also known as BMS-936559, is an anti-PD-L1 antibody described in WO2007/005874. MED14736 is an anti-PD-L1 monoclonal antibody described in WO2011/066389 and US2013/034559. MDX-1106, also known as MDX-1106-04, ONO-4538, BMS-936558, or nivolumab, is an anti-PD-1 antibody described in WO2006/121168. MK-3475, also known as lambrolizumab, is an anti-PD-1 antibody described in WO2009/114335. AMP-224, also known as B7-DCIg, is a PD-L2-Fc fusion soluble receptor described in WO2010/027827 and WO2011/066342.

In some embodiments, the PD-1 axis binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and $(Fab')_2$ fragments. In some embodiments, the anti-PD-L1 antibody is a humanized antibody. In some embodiments, the anti-PD-L1 antibody is a human antibody.

Examples of anti-PD-L1 antibodies useful for the methods of this invention, and methods for making thereof are described in PCT patent application WO 2010/077634, WO 2007/005874, WO 2011/066389, and US 2013/034559, which are incorporated herein by reference. The anti-PD-L1 antibodies useful in this invention, including compositions containing such antibodies, may be used in combination with a taxane to treat cancer.

Anti-PD-1 Antibodies

In some embodiments, the anti-PD-1 antibody is MDX-1106. Alternative names for "MDX-1106" include MDX-1106-04, ONO-4538, BMS-936558, or nivolumab. In some embodiments, the anti-PD-1 antibody is nivolumab (CAS Registry Number: 946414-94-4). In a still further embodiment, provided is an isolated anti-PD-1 antibody comprising a heavy chain variable region comprising the heavy chain variable region amino acid sequence from SEQ ID NO:1 and/or a light chain variable region comprising the light chain variable region amino acid sequence from SEQ ID NO:2. In a still further embodiment, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                      (SEQ ID NO: 1)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK,
```

(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 2)
EIVLTQSPATLSLSPGERATLSCRASQSVSSYLAVVYQQKPGQAPRLLI

YDASNRATGIPARFSGSGSGTDFTLTISSLEPEDFAVYYCQQSSNWPRT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC.

Anti-PD-L1 Antibodies

In some embodiments, the antibody in the formulation comprises at least one tryptophan (e.g., at least two, at least three, or at least four) in the heavy and/or light chain sequence. In some embodiments, amino acid tryptophan is in the HVR regions, framework regions and/or constant regions of the antibody. In some embodiments, the antibody comprises two or three tryptophan residues in the HVR regions. In some embodiments, the antibody in the formulation is an anti-PD-L1 antibody. PD-L1 (programmed death ligand 1), also known as PDL1, B7-H1, B7-4, CD274, and B7-H, is a transmembrane protein, and its interaction with PD-1 inhibits T-cell activation and cytokine production. In some embodiments, the anti-PD-L1 antibody described herein binds to human PD-L1. Examples of anti-PD-L1 antibodies that can be used in the methods described herein are described in PCT patent application WO 2010/077634 A1 and U.S. Pat. No. 8,217,149, which are incorporated herein by reference in their entirety.

In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody.

Anti-PD-L1 antibodies described in WO 2010/077634 A1 and U.S. Pat. No. 8,217,149 may be used in the methods described herein. In some embodiments, the anti-PD-L1 antibody comprises a heavy chain variable region sequence of SEQ ID NO:3 and/or a light chain variable region sequence of SEQ ID NO:4. In a still further embodiment, provided is an isolated anti-PD-L1 antibody comprising a heavy chain variable region and/or a light chain variable region sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 3)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSA, and
(b) the light chain sequence has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 4)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR.

In one embodiment, the anti-PD-L1 antibody comprises a heavy chain variable region comprising an HVR-H1, HVR-H2 and HVR-H3 sequence, wherein:

(a)
(SEQ ID NO: 5)
the HVR-H1 sequence is GFTFSX$_1$SWIH;

(b)
(SEQ ID NO: 6)
the HVR-H2 sequence is AWIX$_2$PYGGSX$_3$YYADSVKG;

(c)
(SEQ ID NO: 7)
the HVR-H3 sequence is RHWPGGFDY;

further wherein: X$_1$ is D or G; X$_2$ is S or L; X$_3$ is T or S.
In one specific aspect, X$_1$ is D; X$_2$ is S and X$_3$ is T.

In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

HC-FR1 is
(SEQ ID NO: 8)
EVQLVESGGGLVQPGGSLRLSCAAS

HC-FR2 is
(SEQ ID NO: 9)
WVRQAPGKGLEWV

HC-FR3 is
(SEQ ID NO: 10)
RFTISADTSKNTAYLQMNSLRAEDTAVYYCAR

HC-FR4 is
(SEQ ID NO: 11)
WGQGTLVTVSA.

In a still further aspect, the heavy chain polypeptide is further combined with a variable region light chain comprising an HVR-L1, HVR-L2 and HVR-L3, wherein:

(a) the HVR-L1 sequence is
(SEQ ID NO: 12)
RASQX$_4$X$_5$X$_6$TX$_7$X$_8$A;

(b) the HVR-L2 sequence is
(SEQ ID NO: 13)
SASX$_9$LX$_{10}$5,;

(c) the HVR-L3 sequence is
(SEQ ID NO: 14)
QQX$_{11}$X$_{12}$X$_{13}$X$_{14}$PX$_{15}$T;

wherein: X$_4$ is D or V; X$_5$ is V or I; X$_6$ is S or N; X$_7$ is A or F; X$_8$ is V or L; X$_9$ is F or T; X$_{10}$ is Y or A; X$_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A.

In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
LC-FR1 is
                             (SEQ ID NO: 15)
DIQMTQSPSSLSASVGDRVTITC

LC-FR2 is
                             (SEQ ID NO: 16)
WYQQKPGKAPKLLIY

LC-FR3 is
                             (SEQ ID NO: 17)
GVPSRFSGSGSGTDFTLTISSLQPEDFATYYC

LC-FR4 is
                             (SEQ ID NO: 18)
FGQGTKVEIKR.
```

In another embodiment, provided is an isolated anti-PD-L1 antibody or antigen binding fragment comprising a heavy chain and a light chain variable region sequence, wherein:

(a) the heavy chain comprises an HVR-H1, HVR-H2 and HVR-H3, wherein further:

```
    (i) the HVR-H1 sequence is
                             (SEQ ID NO: 5)
    GFTFSX₁SWIH;

(ii) the HVR-H2 sequence is
                             (SEQ ID NO: 6)
    AWIX₂PYGGSX₃YYADSVKG (iii) the HVR-H3 sequence is
                             (SEQ ID NO: 7)
    RHWPGGFDY, and
```

(b) the light chain comprises an HVR-L1, HVR-L2 and HVR-L3, wherein further:

```
    (i) the HVR-L1 sequence is
                             (SEQ ID NO: 12)
    RASQX₄X₅X₆TX₇X₈A (ii) the HVR-L2 sequence is
                             (SEQ ID NO: 13)
    SASX₉LX₁₀S; and (iii) the HVR-L3 sequence is
                             (SEQ ID NO: 14)
    QQX₁₁X₁₂X₁₃X₁₄PX₁₅T;
``` wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a $V_H$ subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:

(a) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, or (b) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYHPAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PD-L1 antibody comprising a heavy chain and a light chain variable region sequence, wherein:
(a) the heavy chain sequence has at least 85% sequence identity to the heavy chain sequence:

```
                                       (SEQ ID NO: 25)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS,
``` and/or
(b) the light chain sequences has at least 85% sequence identity to the light chain sequence:

```
                                        (SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSS (SEQ ID NO:27).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                       (SEQ ID NO: 29)
EVQLVESGGGLVQPGGSLRLSCAASGFTFS

HC-FR2
                                       (SEQ ID NO: 30)
WVRQAPGKGLEWVA

HC-FR3
                                       (SEQ ID NO: 10)
RFTISADTSKNTAYLQMNSLRAEDTAVYYCAR

HC-FR4
                                       (SEQ ID NO: 27)
WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                       (SEQ ID NO: 15)
DIQMTQSPSSLSASVGDRVTITC

LC-FR2
                                       (SEQ ID NO: 16)
WYQQKPGKAPKLLIY

LC-FR3
                                       (SEQ ID NO: 17)
GVPSRFSGSGSGTDFTLTISSLQPEDFATYYC
```

```
              LC-FR4
                                      (SEQ ID NO: 28)
              FGQGTKVEIK.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:
(c) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, and/or
(d) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYHPAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSSASTK (SEQ ID NO:31).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18. In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:
(a) the heavy chain sequence has at least 85% sequence identity to the heavy chain sequence:

```
                                      (SEQ ID NO: 26)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTK,
```
or
(b) the light chain sequences has at least 85% sequence identity to the light chain sequence:

```
                                       (SEQ ID NO: 4)
DIQMTQSPSSLSASVGDRVTITCRASQDVSTAVAVWQQKPGKAPKLLIYS

ASFLYSGVPSRFSGSGSGTDFTLTISSLQPEDFATYYCQQYLYHPATFGQ

GTKVEIKR.
```

In some embodiments, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO:4. In some embodiments, provided is an isolated anti-PD-L1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO:26. In some embodiments, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:4 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:26. In some embodiments, one, two, three, four or five amino acid residues at the N-terminal of the heavy and/or light chain may be deleted, substituted or modified.

In a still further embodiment, provided is an isolated anti-PD-L1 antibody comprising a heavy chain and a light chain sequence, wherein:
(a) the heavy chain sequence has at least 85% sequence identity to the heavy chain sequence:

(SEQ ID NO: 32)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNVVYVDGVEVHNAKTKPREEQYAS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPG, (b) the light chain sequences has at least 85% sequence identity to the light chain sequence:

(SEQ ID NO: 33)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some embodiments, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33. In some embodiments, provided is an isolated anti-PD-L1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32. In some embodiments, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32.

In some embodiments, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the embodiments herein, the isolated anti-PD-L1 antibody can bind to a human PD-L1, for example a human PD-L1 as shown in UniProtKB/Swiss-Prot Accession No. Q9NZQ7.1, or a variant thereof.

In a still further embodiment, provided is an isolated nucleic acid encoding any of the antibodies described herein. In some embodiments, the nucleic acid further comprises a vector suitable for expression of the nucleic acid encoding any of the previously described anti-PD-L1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment.

III. Antibody Preparation

The antibodies described herein are prepared using techniques available in the art for generating antibodies, exemplary methods of which are described in more detail in the following sections.

The antibody is directed against an antigen of interest (e.g., PD1 (such as human PD-1), PD-L1 (such as a human PD-L1), PD-L2 (such as human PD-L2), etc.). Preferably, administration of the antibody to a mammal suffering from a disorder can result in a therapeutic benefit in that mammal.

In certain embodiments, an antibody provided herein has a dissociation constant (Kd) of ≤1 µM, ≤150 nM, ≤100 nM, ≤50 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest. The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at approximately 10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (approximately 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(i) Antigen Preparation

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (i.p.) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the invention can be made using the hybridoma method first described by Kohler et al., Nature, 256:495 (1975), and further described, for example, in Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), and Ni, Xiandai Mianyixue, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, Histology and Histopathology, 20(3):927-937 (2005) and Vollmers and Brandlein, Methods and Findings in Experimental and Clinical Pharmacology, 27(3):185-91 (2005).

For various other hybridoma techniques, see, for example, U.S. Patent Publication Nos. 2006/258841; 2006/183887 (fully human antibodies), 2006/059575; 2005/287149; 2005/100546; and 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (SC) or intraperitoneal (IP) injections of a polypeptide of the invention or a fragment thereof, and an adjuvant, such as monophosphoryl lipid A (MPL)/trehalose dicrynomycolate (TDM) (Ribi Immunochem. Research, Inc., Hamilton, MT). A polypeptide of the invention (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, Monoclonal Antibodies:

*Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the invention. The binding specificity of monoclonal antibodies produced by hybridoma cells may be determined by immunoprecipitation or by an in vitro binding assay, such as radioimmunoassay (RIA) or enzyme-linked immunosorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, DMEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Additional methods are reviewed, e.g., in Hoogenboom et al., in *Methods in Molecular Biology* 178:1-37 (O'Brien et al., ed., Human Press, Totowa, NJ, 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

(iv) Chimeric, Humanized and Human Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines have been described for the production of human monoclonal antibodies have been described. (See, e.g., Kozbor J. Immunol., 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See, for example, WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering,* ed. Borrebaeck, supra. The antibody fragment may also be a "linear antibody," e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full-length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (see, e.g., Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

One approach known in the art for making bispecific antibodies is the "knobs-into-holes" or "protuberance-into-cavity" approach (see, e.g., U.S. Pat. No. 5,731,168). In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity" (these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in the following table. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE 1

Properties of amino acid residues

| Amino acid | One-letter abbreviation | Mass[a] (daltons) | Volume[b] (Å$^3$) | Accessible surface area[c] (Å$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43$^{rd}$ ed. Cleveland, Chemical Rubber Publishing Co., 1961.
[b]Values from A. A. Zamyatnin, Prog. Biophys. Mol. Biol. 24: 107-123, 1972.
[c]Values from C. Chothia, J. Mol. Biol. 105: 1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human IgG$_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE 2

Exemplary sets of corresponding knob-and hole-forming mutations

| CH3 of first immunoglobulin | CH3 of second immunoglobulin |
|---|---|
| T366Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

Mutations are denoted by the original residue, followed by the position using the Kabat numbering system, and then the import residue (all residues are given in single-letter amino acid code).
Multiple mutations are separated by a colon.

In some embodiments, an immunoglobulin polypeptide comprises a CH3 domain comprising one or more amino acid substitutions listed in Table 2 above. In some embodiments, a bispecific antibody comprises a first immunoglobulin polypeptide comprising a CH3 domain comprising one or more amino acid substitutions listed in the left column of Table 2, and a second immunoglobulin polypeptide comprising a CH3 domain comprising one or more corresponding amino acid substitutions listed in the right column of Table 2.

Following mutation of the DNA as discussed above, polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31: 753-758, 2013. Modified immunoglobulin polypeptides may be produced using prokaryotic host cells, such as *E. coli*, or eukaryotic host cells, such as CHO cells. Corresponding knob-and-hole-bearing immunoglobulin polypeptides may be expressed in host cells in co-culture and purified together as a heteromultimer, or they may be expressed in single cultures, separately purified, and assembled in vitro. In some embodiments, two strains of bacterial host cells (one expressing an immunoglobulin polypeptide with a knob, and the other expressing an immunoglobulin polypeptide with a hole) are co-cultured using standard bacterial culturing techniques known in the art. In some embodiments, the two strains may be mixed in a specific ratio, e.g., so as to achieve equal expression levels in culture. In some embodiments, the two strains may be mixed in a 50:50, 60:40, or 70:30 ratio. After polypeptide expression, the cells may be lysed together, and protein may be extracted. Standard techniques known in the art that allow for measuring the abundance of homo-multimeric vs. hetero-multimeric species may include size exclusion chromatography. In some embodiments, each modified immunoglobulin polypeptide is expressed separately using standard recombinant techniques, and they may be assembled together in vitro. Assembly may be achieved, for example, by purifying each modified immunoglobulin polypeptide, mixing and incubating them together in equal mass, reducing disulfides (e.g., by treating with dithiothreitol), concentrating, and reoxidizing the polypeptides. Formed bispecific antibodies may be purified using standard techniques including cation-exchange chromatography and measured using standard techniques including size exclusion chromatography. For a more detailed description of these methods, see Speiss et al., *Nat. Biotechnol.* 31:753-8, 2013. In some embodiments, modified immunoglobulin polypeptides may be expressed separately in CHO cells and assembled in vitro using the methods described above.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain ($V_H$) and a variable light chain ($V_L$) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

Antibodies with more than two valencies are contemplated. For example, trispecific antibodies can be prepared. See, e.g., Tuff et al. *J. Immunol.* 147: 60 (1991).

(vii) Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Substitution, Insertion, and Deletion Variants

In Certain Embodiments, Antibody Variants Having One or More Amino Acid Substitutions are provided. Sites of interest for substitutional mutagenesis include the HVRs and FRs. Preferred substitutions are shown in Table 3 under the heading of "preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

Exemplary Substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

a. hydrophobic: Norleucine, Met, Ala, Val, Leu, Ile;
b. neutral hydrophilic: Cys, Ser, Thr, Asn, Gln;

c. acidic: Asp, Glu;
d. basic: His, Lys, Arg;
e. residues that influence chain orientation: Gly, Pro;
f. aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

(x) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided comprising an Fc region wherein a carbohydrate structure attached to the Fc region has reduced fucose or lacks fucose, which may improve ADCC function. Specifically, antibodies are contemplated herein that have reduced fusose relative to the amount of fucose on the same antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In certain embodiments, the antibody is one wherein less than about 50%, 40%, 30%, 20%, 10%, or 5% of the N-linked glycans thereon comprise fucose. For example, the amount of fucose in such an antibody may be from 1% to 80%, from 1% to 65%, from 5% to 65% or from 20% to 40%. In certain embodiments, the antibody is one wherein none of the N-linked glycans thereon comprise fucose, i.e., wherein the antibody is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; US 2005/0123546, and Ferrara et al., Biotechnology and Bioengineering, 93(5): 851-861 (2006). Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

In certain embodiments, the antibody variants comprising an Fc region described herein are capable of binding to an FcγRIII. In certain embodiments, the antibody variants comprising an Fc region described herein have ADCC activity in the presence of human effector cells or have increased ADCC activity in the presence of human effector cells compared to the otherwise same antibody comprising a human wild-type IgG1Fc region.

(xi) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. *Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg et al., *Blood* 101:1045-1052 (2003); and Cragg et al, *Blood* 103:2738-2743 (2004)). FcRn binding and in vivo clearance/half life determinations can also be performed using methods known in the art (see, e.g., Petkova et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues). In an exemplary embodiment, the antibody comprising the following amino acid substitutions in its Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.)). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

(xii) Antibody Derivatives

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(xiii) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2p, plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(q) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology*, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* $24:210^{-215}$ (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells.

Plant cell cultures of cotton, corn, potato, soybean, *petunia*, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xiv) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

(xv) Selecting Biologically Active Antibodies

Antibodies produced as described above may be subjected to one or more "biological activity" assays to select an antibody with beneficial properties from a therapeutic perspective or selecting formulations and conditions that retain biological activity of the antibody. The antibody may be tested for its ability to bind the antigen against which it was raised. For example, methods known in the art (such as ELISA, Western Blot, etc.) may be used.

For example, for an anti-PD-L1 antibody, the antigen binding properties of the antibody can be evaluated in an assay that detects the ability to bind to PD-L1. In some embodiments, the binding of the antibody may be determined by saturation binding; ELISA; and/or competition assays (e.g. RIA's), for example. Also, the antibody may be subjected to other biological activity assays, e.g., in order to evaluate its effectiveness as a therapeutic. Such assays are known in the art and depend on the target antigen and intended use for the antibody. For example, the biological effects of PD-L1 blockade by the antibody can be assessed in CD8+ T cells, a lymphocytic choriomeningitis virus (LCMV) mouse model and/or a syngeneic tumor model e.g., as described in U.S. Pat. No. 8,217,149.

To screen for antibodies which bind to a particular epitope on the antigen of interest (e.g., those which block binding of the anti-PD-L1 antibody of the example to PD-L1), a routine cross-blocking assay such as that described in Antibodies, *A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

IV. Pharmaceutical Compositions and Formulations

Also provided herein are pharmaceutical compositions and formulations comprising a PD-1 axis binding antagonist and/or an antibody described herein (such as an anti-PD-1 antibody or anti-PD-L1 antibody) and, optionally, a pharmaceutically acceptable carrier.

Pharmaceutical compositions and formulations as described herein can be prepared by mixing the active ingredient(s) (e.g., a PD-1 axis binding antagonist) having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The compositions and formulations herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, e.g., anti-PD1 antibody or anti-PD-L1 antibody, which matrices are in the form of shaped articles, e.g.

films, or microcapsules. The formulations to be used for in vivo administration are generally sterile. Sterility may be readily accomplished, e.g., by filtration through sterile filtration membranes.

IV. Methods of Treatment

Provided herein are methods for treating or delaying progression of a cancer (e.g., melanoma) in an individual comprising administering to the individual an effective amount of a PD-1 axis binding antagonist, wherein the ratio between Granzyme B$^+$ CD4$^+$ T cells and FOXP3$^+$ CD4$^+$ T cells in a blood sample obtained from the patient has been determined to be 1 or greater. In some embodiments, the treatment results in a response in the individual after treatment. In some embodiments, the response is a partial response. In some embodiments, the response is a complete response. In some embodiments, the treatment results in a sustained response (e.g., a sustained partial response or complete response) in the individual after cessation of the treatment. The methods described herein may find use in treating conditions where enhanced immunogenicity is desired such as increasing tumor immunogenicity for the treatment of cancer. Also provided herein are methods of enhancing immune function in an individual having melanoma comprising administering to the individual an effective amount of a PD-1 axis binding antagonist (e.g., Nivolomab, Pembrolizumab, Atezolizumab, or Avelumab). Any of the PD-1 axis binding antagonists known in the art or described herein may be used in the methods.

In some instances, the methods provided herein include administration of an effective amount of a PD-1 axis binding antagonist is selected from the group consisting of a PD-1 binding antagonist, a PD-L1 binding antagonist, and a PD-L2 binding antagonist. In some instances, the PD-L1 binding antagonist is an antibody, such as an antibody that is capable of inhibiting PD-L1 binding to PD-1 and B7.1, but does not disrupt binding of PD-1 to PD-L2. In some instances, the PD-L1 binding antagonist antibody is MPDL3280A, which may be administered at a dose of about 700 mg to about 900 mg every two weeks (e.g., about 750 mg to about 900 mg every two weeks, e.g., about 800 mg to about 850 mg every two weeks). In some embodiments, MPDL3280A is administered at a dose of about 840 mg every two weeks.

As a general proposition, the therapeutically effective amount of a PD-1 axis binding antagonist (e.g., an anti-PD-L1 antibody, e.g., MPDL3280A) may be administered to a human will be in the range of about 0.01 to about 50 mg/kg of patient body weight whether by one or more administrations. In some embodiments, for example, the antagonist (e.g., anti-PD-L1 antibody, e.g., MPDL3280A) is administered in a dose of about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antagonist (e.g., anti-PD-L1 antibody, e.g., MPDL3280A) is administered at 15 mg/kg. However, other dosage regimens may be useful. In one embodiment, a PD-1 axis binding antagonist (e.g., anti-PD-L1 antibody, e.g., MPDL3280A) is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, or about 1500 mg. In some embodiments, a PD-1 axis binding antagonist (e.g., anti-PD-L1 antibody, e.g., MPDL3280A) is administered at a dose of about 800 mg to about 850 mg every two weeks. In some embodiments, a PD-1 axis binding antagonist (e.g., anti-PD-L1 antibody, e.g., MPDL3280A) is administered at a dose of about 840 mg every two weeks. The dose may be administered as a single dose or as multiple doses (e.g., 2 or 3 doses), such as infusions. The dose of the antibody administered in a combination treatment may be reduced as compared to a single treatment. In some embodiments, for example, the method for treating or delaying progression of locally advanced or metastatic breast cancer in an individual comprises a dosing regimen comprising treatment cycles, wherein the individual is administered, on days 1 and 15 of each cycle, a human PD-1 axis binding antagonist (e.g., anti-PD-L1 antibody, e.g., MPDL3280A) at a dose of about 840 mg, wherein each cycle is 28 days (i.e., each cycle is repeated every 28 days).

The progress of this therapy is monitored by the methods described herein. In some embodiment, the size of the cytotoxic Granzyme B$^+$ CD4+ T cell population within the CD4+ T cell population is predictive of durability of response. For example, a patient that was observed as disease free for 3 months had a ratio of Granzyme B$^+$ CD4$^+$ T cells and Tregs of 4 while a patient that was observed as disease free for 6 months had ratio of 45. A larger population size of Granzyme B$^+$ CD4$^+$ T cells, thus, was indicative of longer disease free response.

In some embodiments, the methods further comprise administering an effective amount of at least one further therapeutic agent.

In some embodiments, the further therapeutic agent is an agent targeting the PI3K/AKT/mTOR pathway, HSP90 inhibitor, tubulin inhibitor, apoptosis inhibitor, and/or chemopreventative agent. The further therapeutic agent may be one or more of the chemotherapeutic agents described herein. In some instances, the chemotherapeutic agent is a platinum-based chemotherapeutic agent, such as carboplatin.

In some instances, the chemotherapeutic agent is a taxane (e.g., nab-paclitaxel (ABRAXANE®), paclitaxel, or docetaxel). In some instances, the taxane is nab-paclitaxel (ABRAXANE®). In some instances, the nab-paclitaxel (ABRAXANE®) is administered to the individual at a dose of about 100 mg/m$^2$ to about 125 mg/m$^2$ every week. In some instances, the nab-paclitaxel (ABRAXANE®) is administered to the individual at a dose of about 100 mg/m$^2$ every week. As a general proposition, the therapeutically effective amount of a taxane (e.g., nab-paclitaxel (ABRAXANE®)) administered to a human will be in the range of about 25 to about 300 mg/m$^2$ (e.g., about 25 mg/m$^2$, about 50 mg/m$^2$, about 75 mg/m$^2$, about 100 mg/m$^2$, about 125 mg/m$^2$, about 150 mg/m$^2$, about 175 mg/m$^2$, about 200 mg/m$^2$, about 225 mg/m$^2$, about 250 mg/m$^2$, about 275 mg/m$^2$, or about 300 mg/m$^2$), whether by one or more administrations. For example, in some embodiments, about 100 mg/m$^2$ of nab-paclitaxel (ABRAXANE®) is administered. In some embodiments, nab-paclitaxel (ABRAXANE®) is administered at 100 mg/m$^2$ once a week. In some embodiments, about 125 mg/m$^2$ of paclitaxel is administered. In some embodiments, paclitaxel is administered at 200 mg/m$^2$ every three weeks. In some embodiments, the taxane (e.g., nab-paclitaxel (ABRAXANE®)) may be administered weekly, every 2 weeks, every 3 weeks, every 4 weeks, on days 1, 8 and 15 of each 21-day cycle, or on days 1, 8, and 15 of each 28-day cycle.

In some instances, the PD-1 axis binding antagonist (e.g., an anti-PD-L1 antibody, e.g., MPDL3280A) and the taxane (e.g., nab-paclitaxel (ABRAXANE®)) are administered in a single dosing regimen. The administration of these agents may be concurrent or separate within the context of the dosing regimen. For example, in some instances, the methods provided herein include a dosing regimen comprising treatment cycles, wherein the individual is administered, on days 1 and 15 of each cycle, a human PD-1 axis binding antagonist at a dose of about 840 mg, and on days 1, 8, and 15 of each cycle, a taxane at a dose of about 100 mg/m$^2$, each cycle being repeated every 28 days.

In some embodiments, the individual is a human. In some embodiments, the individual is suffering from melanoma. In some embodiments, the individual is suffering from lung cancer, e.g., non-s, all cell lung cancer. In some embodiments, the individual is a human. In some embodiments, the individual is suffering from pancreatic cancer. In some embodiments, the individual is a human. In some embodiments, the individual is suffering from gastric cancer. In some embodiments, the individual is a human. In some embodiments, the individual is suffering from colorectal cancer. In some embodiments, the individual is a human. In some embodiments, the individual is suffering from renal cell carcinoma. In some embodiments, the individual is a human. In some embodiments, the individual is suffering from pancreatic cancer. In some embodiments, the individual is suffering from locally advanced or metastatic breast cancer. In some embodiments, the metastatic breast cancer is mTNBC. In some embodiments, the individual has had two or fewer prior cytotoxic treatment regimens for cancer. In some embodiments, the individual has never had prior targeted systemic treatment for cancer. In some embodiments, the individual has cancer that is resistant to one or more cancer therapies. In some embodiments, resistance to cancer therapy includes recurrence of cancer or refractory cancer. Recurrence may refer to the reappearance of cancer, in the original site or a new site, after treatment. In some embodiments, resistance to a cancer therapy includes progression of the cancer during treatment with the anti-cancer therapy. In some embodiments, resistance to a cancer therapy includes cancer that does not response to treatment. The cancer may be resistant at the beginning of treatment or it may become resistant during treatment. In some embodiments, the cancer is at early stage or at late stage.

The PD-1 axis binding antagonist and the second therapeutic agent, e.g., taxane (e.g., nab-paclitaxel (ABRAXANE®)) may be administered in any suitable manner known in the art. For example, the PD-1 axis binding antagonist and the second therapeutic agent, e.g., taxane may be administered sequentially (at different times) or concurrently (at the same time). In some embodiments, the PD-1 axis binding antagonist is in a separate composition as the second therapeutic agent. In some embodiments, the PD-1 axis binding antagonist is in the same composition as the second therapeutic agent.

In some embodiments, the PD-1 axis binding antagonist and the second therapeutic agent, e.g., chemotherapeutic agent, e.g., taxane, may be administered by the same route of administration or by different routes of administration. In some embodiments, the PD-1 axis binding antagonist is administered intravenously, intramuscularly, subcutaneously, topically, orally, transdermally, intraperitoneally, intraorbitally, by implantation, by inhalation, intrathecally, intraventricularly, or intranasally. In some embodiments, the taxane is administered intravenously, intramuscularly, subcutaneously, topically, orally, transdermally, intraperitoneally, intraorbitally, by implantation, by inhalation, intrathecally, intraventricularly, or intranasally. An effective amount of the PD-1 axis binding antagonist, and, optionally, the second therapeutic agent, may be administered for prevention or treatment of disease. The appropriate dosage of the PD-1 axis binding antagonist and/or the second therapeutic agent may be determined based on the type of disease to be treated, the type of the PD-1 axis binding antagonist and the second therapeutic agent, the severity and course of the disease, the clinical condition of the individual, the individual's clinical history and response to the treatment, and the discretion of the attending physician.

In some embodiments, the methods may further comprise an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation.

In some embodiments, the methods further comprise administering a platinum-based chemotherapeutic agent with the PD-1 axis binding antagonist and taxane. In some embodiments, the platinum-based chemotherapeutic agent is carboplatin. Dosages and administration of carboplatin are well-known in the art. An exemplary dosage of carboplatin is administered with a target area under the curve (AUC) of 6 mg/ml. In some embodiments, the carboplatin is administered intravenously every 3 weeks.

Without wishing to be bound to theory, it is thought that enhancing T cell stimulation, by promoting an activating co-stimulatory molecule or by inhibiting a negative co-stimulatory molecule, may promote tumor cell death thereby treating or delaying progression of cancer. In some embodiments, a PD-1 axis binding antagonist (e.g., anti-PD-1, e.g. MDX-1106 (Nivolumab, Bristol-Myers Squibb) or MK-3475 (Pembrolizumab, Merck), or anti-PD-L1 antibody, e.g., MPDL3280A (Atezolizumab) or Avelumab) may be administered in conjunction with an agonist directed against an activating co-stimulatory molecule. In some embodiments, an activating co-stimulatory molecule may include CD40, CD226, CD28, OX40, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, a PD-1 axis binding antagonist (e.g., anti-PD-1, e.g. MDX-1106 or MK-3475, or anti-PD-L1 antibody, e.g., MPDL3280A) may be administered in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3, B7-H3, B7-H4, IDO, TIGIT, MICA/B, or arginase.

In some embodiments, a PD-1 axis binding antagonist (e.g., anti-PD-1, e.g. MDX-1106 or MK-3475, or anti-PD-L1 antibody, e.g., MPDL3280A) may be administered in conjunction with an antagonist directed against CTLA-4 (also known as CD152), for example, a blocking antibody. In some embodiments, a PD-1 axis binding antagonist may be administered in conjunction with ipilimumab (also known as MDX-010, MDX-101, or YERVOY®). In some embodiments, a PD-1 axis binding antagonist may be administered in conjunction with tremelimumab (also known as ticilimumab or CP-675,206). In some embodiments, a PD-1 axis binding antagonist may be administered in conjunction with an antagonist directed against B7-H3 (also known as CD276), for example, a blocking antibody. In some embodiments, a PD-1 axis binding antagonist may be administered in conjunction with MGA271. In some embodiments, a PD-1 axis binding antagonist may be administered in conjunction with an antagonist directed against a TGF beta, for example, metelimumab (also known as CAT-192), fresolimumab (also known as GC1008), or LY2157299.

In some embodiments, a PD-1 axis binding antagonist may be administered in conjunction with a treatment comprising adoptive transfer of a T cell (e.g., a cytotoxic T cell or CTL) expressing a chimeric antigen receptor (CAR). In some embodiments, a PD-1 axis binding antagonist may be administered in conjunction with a treatment comprising adoptive transfer of a T cell comprising a dominant-negative TGF beta receptor, e.g, a dominant-negative TGF beta type II receptor. In some embodiments, a PD-1 axis binding antagonist may be administered in conjunction with a treatment comprising a HERCREEM protocol (see, e.g., ClinicalTrials.gov Identifier NCT00889954).

In some embodiments, a PD-1 axis binding antagonist may be administered in conjunction with an agonist directed against CD137 (also known as TNFRSF9, 4-1BB, or ILA), for example, an activating antibody. In some embodiments, a PD-1 axis binding antagonist may be administered in conjunction with urelumab (also known as BMS-663513). In some embodiments, a PD-1 axis binding antagonist and a taxane may be administered in conjunction with an agonist directed against CD40, for example, an activating antibody. In some embodiments, a PD-1 axis binding antagonist and a taxane may be administered in conjunction with CP-870893. In some embodiments, a PD-1 axis binding antagonist and a taxane may be administered in conjunction with an agonist directed against OX40 (also known as CD134), for example, an activating antibody. In some embodiments, a PD-1 axis binding antagonist and a taxane may be administered in conjunction with an anti-OX40 antibody (e.g., AgonOX). In some embodiments, a PD-1 axis binding antagonist and a taxane may be administered in conjunction with an agonist directed against CD27, for example, an activating antibody. In some embodiments, a PD-1 axis binding antagonist and a taxane may be administered in conjunction with CDX-1127. In some embodiments, a PD-1 axis binding antagonist and a taxane may be administered in conjunction with an antagonist directed against indoleamine-2,3-dioxygenase (IDO). In some embodiments, with the IDO antagonist is 1-methyl-D-tryptophan (also known as 1-D-MT).

In some embodiments, a PD-1 axis binding antagonist and a taxane may be administered in conjunction with an antibody-drug conjugate. In some embodiments, the antibody-drug conjugate comprises mertansine or monomethyl auristatin E (MMAE). In some embodiments, a PD-1 axis binding antagonist and a taxane may be administered in conjunction with and anti-NaPi2b antibody-MMAE conjugate (also known as DNIB0600A or RG7599). In some embodiments, a PD-1 axis binding antagonist and a taxane may be administered in conjunction with trastuzumab emtansine (also known as T-DM1, ado-trastuzumab emtansine, or KADCYLA®, Genentech). In some embodiments, a PD-1 axis binding antagonist and a taxane may be administered in conjunction with DMUC5754A. In some embodiments, a PD-1 axis binding antagonist and a taxane may be administered in conjunction with an antibody-drug conjugate targeting the endothelin B receptor (EDNBR), for example, an antibody directed against EDNBR conjugated with MMAE.

In some embodiments, a PD-1 axis binding antagonist and a taxane may be administered in conjunction with an angiogenesis inhibitor. In some embodiments, a PD-1 axis binding antagonist and a taxane may be administered in conjunction with an antibody directed against a VEGF, for example, VEGF-A. In some embodiments, a PD-1 axis binding antagonist (e.g., anti-PD-L1 antibody, e.g., MPDL3280A) and a taxane (e.g., nab-paclitaxel (ABRAXANE®)) may be administered in conjunction with bevacizumab (also known as AVASTIN®, Genentech). In some embodiments, a PD-1 axis binding antagonist and a taxane may be administered in conjunction with an antibody directed against angiopoietin 2 (also known as Ang2). In some embodiments, a PD-1 axis binding antagonist and a taxane may be administered in conjunction with MEDI3617.

In some embodiments, a PD-1 axis binding antagonist and a taxane may be administered in conjunction with an antineoplastic agent. In some embodiments, a PD-1 axis binding antagonist and a taxane may be administered in conjunction with an agent targeting CSF-1R (also known as M-CSFR or CD115). In some embodiments, a PD-1 axis binding antagonist and a taxane may be administered in conjunction with anti-CSF-1R (also known as IMC-CS4). In some embodiments, a PD-1 axis binding antagonist and a taxane may be administered in conjunction with an interferon, for example interferon alpha or interferon gamma. In some embodiments, a PD-1 axis binding antagonist and a taxane may be administered in conjunction with Roferon-A (also known as recombinant Interferon alpha-2a). In some embodiments, a PD-1 axis binding antagonist and a taxane may be administered in conjunction with GM-CSF (also known as recombinant human granulocyte macrophage colony stimulating factor, rhu GM-CSF, sargramostim, or LEUKINE®). In some embodiments, a PD-1 axis binding antagonist and a taxane may be administered in conjunction with IL-2 (also known as aldesleukin or PROLEUKIN®). In some embodiments, a PD-1 axis binding antagonist and a taxane may be administered in conjunction with IL-12. In some embodiments, a PD-1 axis binding antagonist and a taxane may be administered in conjunction with an antibody targeting CD20. In some embodiments, the antibody targeting CD20 is obinutuzumab (also known as GA101 or GAZYVA®) or rituximab. In some embodiments, a PD-1 axis binding antagonist and a taxane may be administered in conjunction with an antibody targeting GITR. In some embodiments, the antibody targeting GITR is TRX518.

In some embodiments, a PD-1 axis binding antagonist and a taxane may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, a PD-1 axis binding antagonist and a taxane may be administered in conjunction with an adjuvant. In some embodiments, a PD-1 axis binding antagonist and a taxane may be administered in conjunction with a treatment comprising a TLR agonist, for example, Poly-ICLC (also known as HIL-TONOL®), LPS, MPL, or CpG ODN. In some embodiments, a PD-1 axis binding antagonist and a taxane may be administered in conjunction with tumor necrosis factor (TNF) alpha. In some embodiments, a PD-1 axis binding antagonist and a taxane may be administered in conjunction with IL-1. In some embodiments, a PD-1 axis binding antagonist and a taxane may be administered in conjunction with HMGB1. In some embodiments, a PD-1 axis binding antagonist and a taxane may be administered in conjunction with an IL-10 antagonist. In some embodiments, a PD-1 axis binding antagonist and a taxane may be administered in conjunction with an IL-4 antagonist. In some embodiments, a PD-1 axis binding antagonist and a taxane may be administered in conjunction with an IL-13 antagonist. In some embodiments, a PD-1 axis binding antagonist and a taxane may be administered in conjunction with an HVEM antagonist. In some embodiments, a PD-1 axis binding antagonist and a taxane may be administered in conjunction with an ICOS agonist, e.g., by administration of ICOS-L, or an agonistic antibody directed against ICOS. In some embodiments, a PD-1 axis binding antagonist and a taxane may be administered in conjunction with a treatment targeting CX3CL1. In some embodiments, a PD-1 axis binding antagonist and a taxane may be administered in conjunction with a treatment targeting CXCL9. In some embodiments, a PD-1 axis binding antagonist and a taxane may be administered in conjunction with a treatment targeting CXCL10. In some embodiments, a PD-1 axis binding antagonist and a taxane may be administered in conjunction with a treatment targeting CCL5. In some embodiments, a PD-1 axis binding antagonist and a taxane may be administered in conjunction with an LFA-1 or ICAM1 agonist. In some embodiments, a PD-1 axis binding antagonist and a taxane may be administered in conjunction with a Selectin agonist.

In some embodiments, a PD-1 axis binding antagonist and a taxane may be administered in conjunction with a targeted therapy. In some embodiments, a PD-1 axis binding antagonist and a taxane may be administered in conjunction with an inhibitor of B-Raf. In some embodiments, a PD-1 axis binding antagonist and a taxane may be administered in conjunction with vemurafenib (also known as ZELBORAF®). In some embodiments, a PD-1 axis binding antagonist and a taxane may be administered in conjunction with dabrafenib (also known as TAFINLAR®). In some embodiments, a PD-1 axis binding antagonist and a taxane may be administered in conjunction with erlotinib (also known as TARCEVA®). In some embodiments, a PD-1 axis binding antagonist and a taxane may be administered in conjunction with an inhibitor of a MEK, such as MEK1 (also known as MAP2K1) or MEK2 (also known as MAP2K2). In some embodiments, a PD-1 axis binding antagonist and a taxane may be administered in conjunction with cobimetinib (also known as GDC-0973 or XL-518). In some embodiments, a PD-1 axis binding antagonist and a taxane may be administered in conjunction with trametinib (also known as MEKINIST®). In some embodiments, a PD-1 axis binding antagonist and a taxane may be administered in conjunction with an inhibitor of K-Ras. In some embodiments, a PD-1 axis binding antagonist and a taxane may be administered in conjunction with an inhibitor of c-Met. In some embodiments, a PD-1 axis binding antagonist and a taxane may be administered in conjunction with onartuzumab (also known as MetMAb). In some embodiments, a PD-1 axis binding antagonist and a taxane may be administered in conjunction with an inhibitor of Alk. In some embodiments, a PD-1 axis binding antagonist and a taxane may be administered in conjunction with AF802 (also known as CH5424802 or alectinib). In some embodiments, a PD-1 axis binding antagonist and a taxane may be administered in conjunction with an inhibitor of a phosphatidylinositol 3-kinase (PI3K). In some embodiments, a PD-1 axis binding antagonist and a taxane may be administered in conjunction with BKM120. In some embodiments, a PD-1 axis binding antagonist and a taxane may be administered in conjunction with idelalisib (also known as GS-1101 or CAL-101). In some embodiments, a PD-1 axis binding antagonist and a taxane may be administered in conjunction with perifosine (also known as KRX-0401). In some embodiments, a PD-1 axis binding antagonist and a taxane may be administered in conjunction with an inhibitor of an Akt. In some embodiments, a PD-1 axis binding antagonist may be administered in conjunction with MK2206. In some embodiments, a PD-1 axis binding antagonist and a taxane may be administered in conjunction with GSK690693. In some embodiments, a PD-1 axis binding antagonist and a taxane may be administered in conjunction with GDC-0941. In some embodiments, a PD-1 axis binding antagonist and a taxane may be administered in conjunction with an inhibitor of mTOR. In some embodiments, a PD-1 axis binding antagonist and a taxane may be administered in conjunction with sirolimus (also known as rapamycin). In some embodiments, a PD-1 axis binding antagonist and a taxane may be administered in conjunction with temsirolimus (also known as CCI-779 or TORISEL®). In some embodiments, a PD-1 axis binding antagonist and a taxane may be administered in conjunction with everolimus (also known as RAD001). In some embodiments, a PD-1 axis binding antagonist and a taxane may be administered in conjunction with ridaforolimus (also known as AP-23573, MK-8669, or deforolimus). In some embodiments, a PD-1 axis binding antagonist and a taxane may be administered in conjunction with OSI-027. In some embodiments, a PD-1 axis binding antagonist and a taxane may be administered in conjunction with AZD8055. In some embodiments, a PD-1 axis binding antagonist and a taxane may be administered in conjunction with INK128. In some embodiments, a PD-1 axis binding antagonist and a taxane may be administered in conjunction with a dual PI3K/mTOR inhibitor. In some embodiments, a PD-1 axis binding antagonist and a taxane may be administered in conjunction with XL765. In some embodiments, a PD-1 axis binding antagonist and a taxane may be administered in conjunction with GDC-0980. In some embodiments, a PD-1 axis binding antagonist and a taxane may be administered in conjunction with BEZ235 (also known as NVP-BEZ235). In some embodiments, a PD-1 axis binding antagonist and a taxane may be administered in conjunction with BGT226. In some embodiments, a PD-1 axis binding antagonist and a taxane may be administered in conjunction with GSK2126458. In some embodiments, a PD-1 axis binding antagonist and a taxane may be administered in conjunction with PF-04691502. In some embodiments, a PD-1 axis binding antagonist and a taxane may be administered in conjunction with PF-05212384 (also known as PKI-587).

The novel methods described herein can be used to determine efficacy of treatment comprising a PD-L1 axis binding antagonist before tumor shrinkage can be detected. Further, the novel methods described herein can be used to determine efficacy of treatment comprising a PD-L1 axis binding antagonist by distinguishing between progressive disease on treatment and pseudoprogression. In some instances, tumor size initially increases following therapy with a treatment comprising a PD-L1 axis binding antagonist. This increase is not, in fact, due to an increase in tumor burden but, rather, the temporary increase in tumor size is a result of the treatment, e.g., an influx and/or expansion of immune cells, commonly referred to as "pseudoprogression." The methods described herein can distinguish between such pseudoprogression and progressive disease.

VI. Articles of Manufacture or Kits

In another embodiment of the invention, an article of manufacture or a kit is provided comprising a PD-1 axis binding antagonist (e.g., anti-PD-L1 antibody, e.g., MPDL3280A) and a package insert comprising instructions for using the PD-1 axis binding antagonist in an individual having a ratio between Granzyme $B^+$ $CD4^+$ T cells and $FOXP3^+$ $CD4^+$ T cells of 1 or greater in a blood sample obtained from the individual or to enhance immune function of an individual a ratio between Granzyme $B^+$ $CD4^+$ T cells and $FOXP3^+$ $CD4^+$ T cells of 1 or greater in a blood sample obtained from the individual. Any of the PD-1 axis binding antagonist described herein may be included in the article of manufacture or kits.

Suitable containers for the article of manufacture or kit include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and antineoplastic agent). Suitable containers for the one or more agent include, for example, bottles, vials, bags and syringes.

The specification is considered to be sufficient to enable one skilled in the art to practice the invention. Various modifications of the invention in addition to those shown and described herein will become apparent to those skilled in the art from the foregoing description and fall within the scope of the appended claims.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

$CD4^+$ T Cells and Allogeneic DCs in mMLR Assay

To unravel the mechanism underlining PD-1 blockade, we developed an in-vitro functional assay focused on $CD4^+$ T cells in which the $CD4^+$ T cells can recognize allogeneic MHCII and mount a detectable immune response. This assay, called minimal MLR (mMLR), we co-cultured sorted CD4 T cells obtained from a healthy donor with monocyte-derived mature dendritic cells from an unrelated donor.

Minimal Mixed Lymphocyte Reaction

Figure 1B:
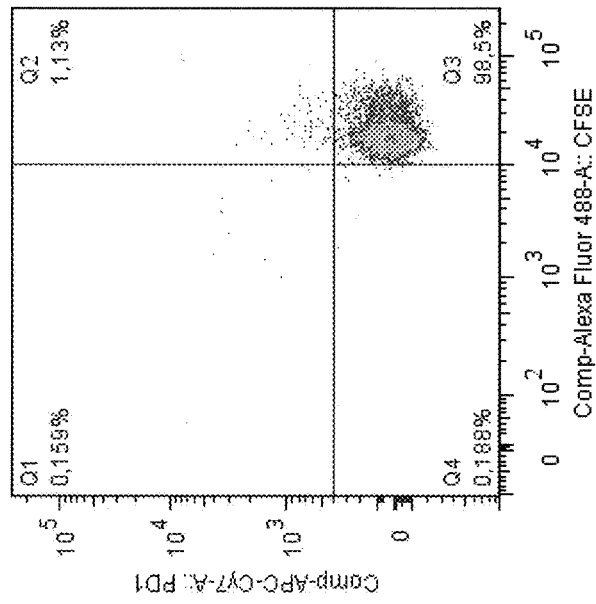
FIG. 1B shows the PD-1 expression profile in allospecific CD4$^+$ T cells identified as the CFSE low population.

We developed an assay in which freshly purified $CD4^+$ T cells are co-cultured for 5 days in the presence of monocyte-derived allogeneic mature dendritic cells (mDCs). Monocytes were isolated from fresh PBMCs one week prior to the co-culture through plastic adherence followed by the removal of the non-adherent cells. We then generated immature DCs (iDCs) from the monocytes by culturing the monocytes for 5 days in media containing GM-CSF (50 ng/ml) and IL-4 (100 ng/ml). To induce iDCs maturation, we added TNF-α, IL-1β and IL-6 (50 ng/ml each) to the culturing media for 2 additional days. We then assessed DCs maturation by measuring their surface expression of Major Histocompatibility Complex Class II (MHCII, eBioscience), CD80, CD83 and CD86 (all from BD Biosciences) through flow cytometry (LSRFortessa, BD Biosciences). On the day of the minimal mixed lymphocyte reaction (mMLR), $CD4^+$ T cells were enriched via a microbead kit (Miltenyi Biotec) from 108 PBMCs obtained from an unrelated donor. Prior culture, $CD4^+$ T cells were labeled with 5 M of Carboxy-Fluorescein-Succinimidyl Esther (CFSE). 105 CD4 T cells were then plated in a 96 well plate U bottom together with mature allo-DCs (5:1) in the presence or absence of blocking anti-PD-1 antibody (either 0376 or MDX-1106 at the concentration of 10 μg/ml. The mMLR allowed us to induce high PD-1 expression levels on most of the allospecific $CD4^+$ T cells by day 5 from the co-culture (FIG. 1).

Statistics corresponds to P<0.01 and * to P<0.001 calculated with one way ANOVA (GraphPad Prism).

Example 2

PD-1 Blockade Increases IFN-γ Secretion and Granzyme B Production by $CD4^+$ T Cells We next determined the effect of an anti-PD-1 blocking antibody added to mMLR cultures as described in Example 1.

Cytokine Intracellular Staining and ELISA

Figure 2:
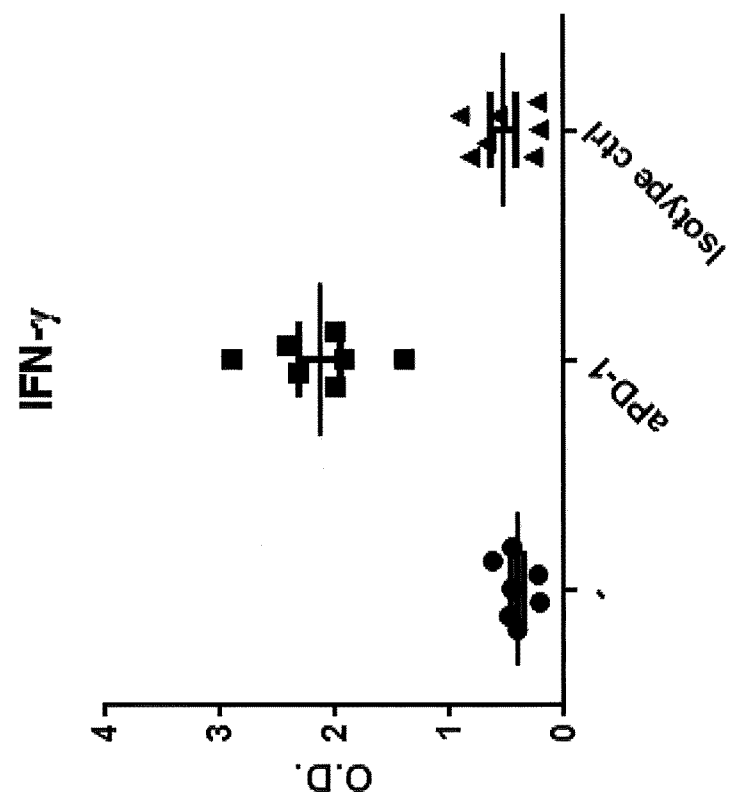
FIG. 2 shows that PD-1 blockade increases IFN-γ secretion by CD4$^+$ T cells. Levels of IFN-γ present in the supernatant of CD4$^+$ T cells cocultured with allo-DCs with or without anti-PD-1 blocking antibody or isotype control. Each data point (circle, square or triangle) represents one donor from each independent experiment.
Figure 3A:
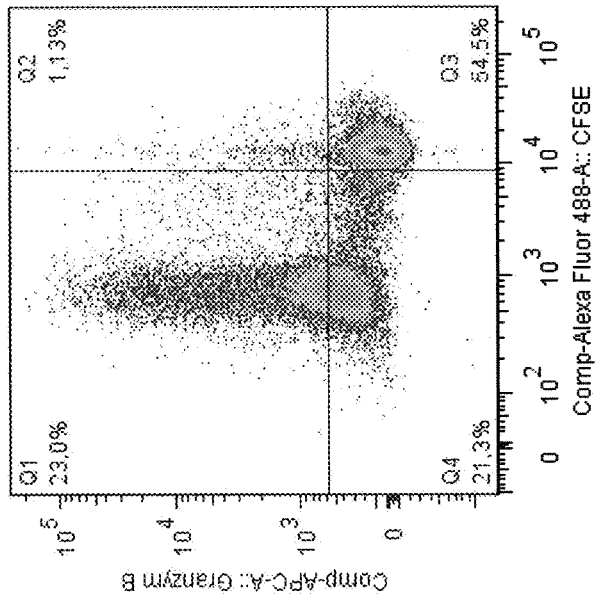
FIGS. 3A-C show that PD-1 blockade increases Granzyme B production by CD4$^+$ T cells.
Figure 3B:
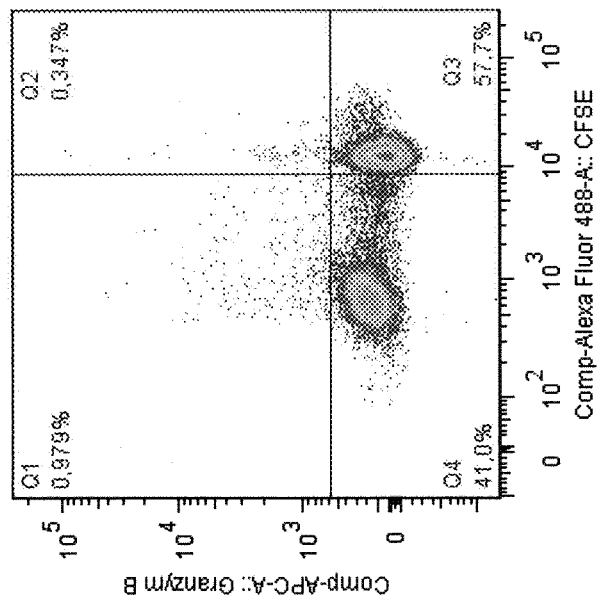
Figure 3C:
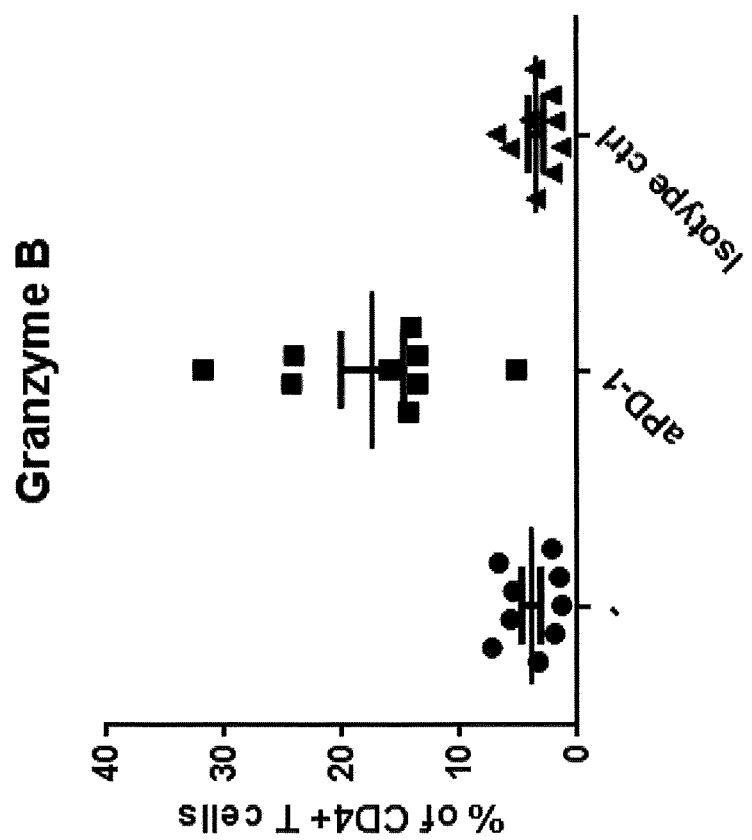

At day 5 from the mMLR co-culture we collected the cell-culture supernatants, used to measure the IFN-γ levels by ELISA (R&D systems, following manufacturer instructions), and left the cells at 37° C. for additional 5 hours in presence of Golgi Plug (Brefeldin A, BD Bioscience) and Golgi Stop (Monensin, BD Bioscience). The cells were then washed, stained on the surface with anti-human CD4 antibody and the Live/Dead fixable dye Aqua (Invitrogen) before being fixed/permeabilized with Fix/Perm Buffer (BD Bioscience). We then performed intracellular staining for Granzyme B (BD Bioscience), IFN-γ and IL-2 (both antibodies from eBioscience). By adding an anti-PD-1 blocking antibody (Roche 0376) at day 1 after co-culture, we could increase the amount of IFN-γ released in the supernatant by day 5, (FIG. 2) and, surprisingly, induce significant Granzyme B production by $CD4^+$ T cells (FIG. 3) when compared to the co-culture alone and in presence of an isotype control.

TABLE 4

Anti-PD-1 antibody 0376 amino acid sequences of HVRs and heavy and light chain variable regions.

| Designation | Sequence | SEQ ID NO. |
|---|---|---|
| heavy chain HVR-H1 | GFSFSSY | 34 |
| heavy chain HVR-H2 | GGR | 35 |
| heavy chain HVR-H3 | TGRVYFALD | 36 |
| light chain HVR-L1 | SESVDTSDNSF | 37 |
| light chain HVR-L2 | RSS | 38 |
| light chain HVR-L3 | NYDVPW | 39 |
| variant-heavy chain variable domain VH | EVQLLESGGGLVQPGGSLRLSCAAS GFSFSSYTMSWVRQAPGKGLEWVAT ISGGGRDIYYPDSVKGRFTISRDNS KNTLYLQMNSLRAEDTAVYYCVLLT GRVYFALDSWGQGTLVTVSS | 40 |
| variant-light chain variable domain VL | DIVMTQSPDSLAVSLGERATINCKA SESVDTSDNSFIHWYQQKPGQSPKL LIYRSSTLESGVPDRFSGSGSGTDF TLTISSLQAEDVAVYYCQQNYDVPW TFGQGTKVEIK | 41 |

TABLE 5

Anti-PD-L1 antibody sequence (PD-L1 muIgG1 DAPG).

| Designation | Sequence | SEQ ID NO. |
|---|---|---|
| Heavy chain | EVQLVESGGGLVQPGGSLRLSCAASGFTFSDSWIHWVRQAPGKGLEW VAWIESPYGGSTYYADSVKGRFTISADTSKNTAYLQMNSLRAEDTAVY YCARRHWPGGFDYWGQGTLVTVSAAKTTPPSVYPLAPGSAAQTNSM VTLGCLVKGYFPEPVTVTWNSGSLSSGVHTFPAVLQSDLYTLSSSVTV PSSTWPSQTVTCNVAHPASSTKVDKKIVPRDCGCKPCICTVPEVSSVFI FPPKPKDVLTITLTPKVTCVVVAISKDDPEVQFSWFVDDVEVHTAQTK PREEQINSTFRSVSELPIMHQDWLNGKEFKCRVNSAAFGAPIEKTISKT KGRPKAPQVYTIPPPKEQMAKDKVSLTCMITNFFPEDITVEWQWNGQP AENYKNTQPIMDTDGSYFVYSKLNVQKSNWEAGNTFTCSVLHEGLHN HHTEKSLSHSPGK | 42 |
| Light chain | DIQMTQSPSSLSASVGDRVTITCRASQDVSTAVAWYQQKPGKAPKLLI YSASFLYSGVPSRFSGSGSGTDFTLTISSLQPEDFATYYCQQYLYHPAT FGQGTKVEIKRADAAPTVSIFPPSSEQLTSGGASVVCFLNNFYPKDINV KWKIDGSERQNGVLNSWTDQDSKDSTYSMSSTLTLTKDEYERHNSYT CEATHKTSTSPIVKSFNRNEC | 43 |

Example 3

Figure 4A:
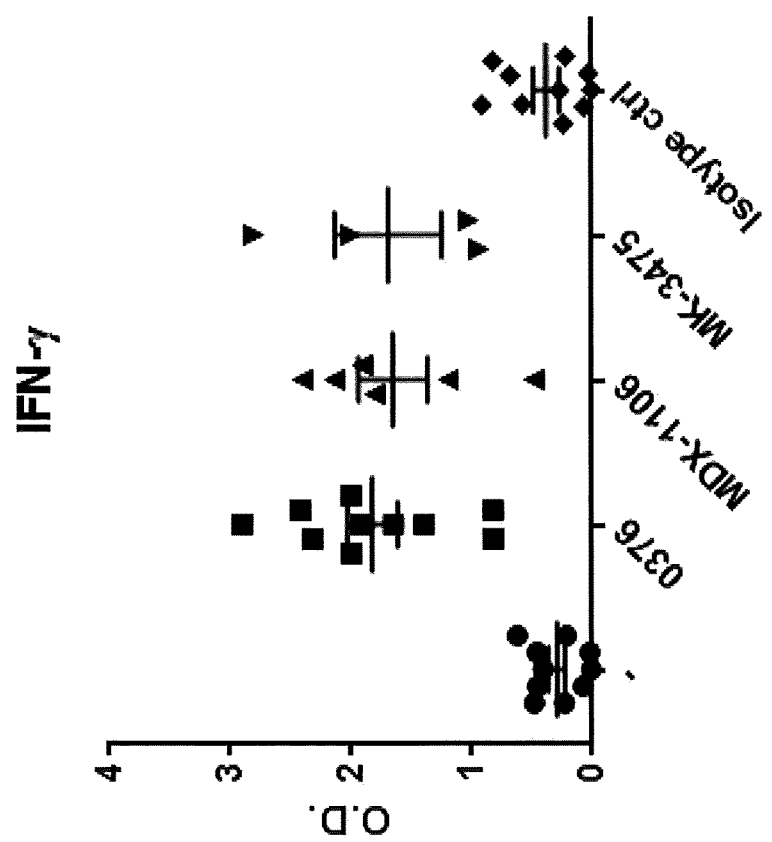
FIGS. 4A-B show a comparison of induction of IFN-γ and Granyme B$^+$ CD4$^+$ T cells with the anti-PD-1 antibodies 0376, MDX-1106 and MK-3475 or isotype control over baseline (no antibody added to the culture, "–"). While the anti-PD-1 antibodies 0376, MDX-1106 and MK-3475 elicit secretion of similar amounts of IFN-γ (FIG. 4A), 0376 is significantly superior in inducing Granyme B$^+$ CD4$^+$ T cells (P=0.02) (FIG. 4B).
Figure 4B:
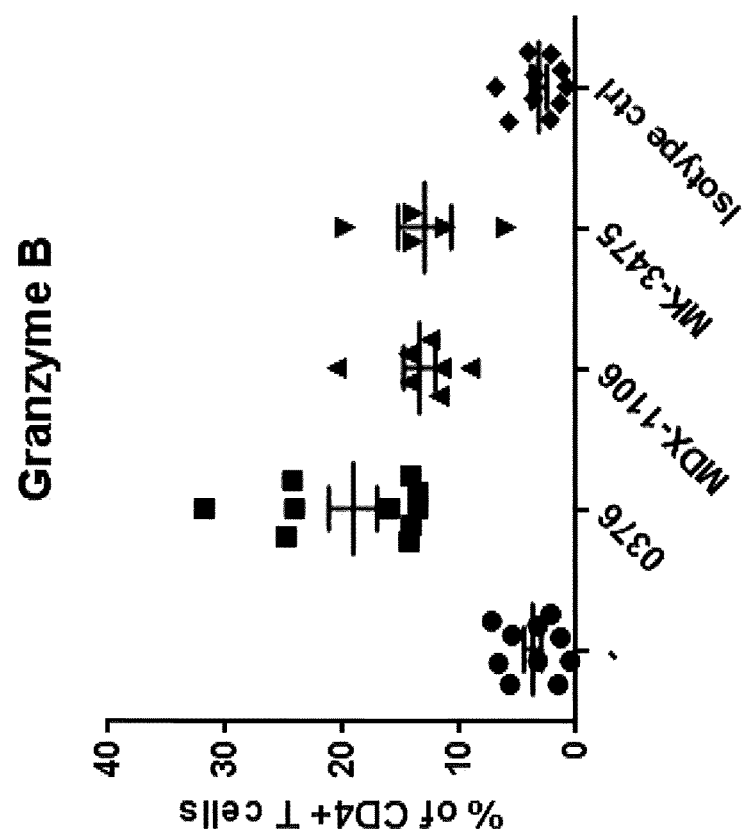

Induction of Cytotoxic CD4+ T Cell in Response to Various Anti-PD-1 Axis Blocking Antibodies The anti-PD-1 antibodies 0376, MDX-1106 (Nivolumab, Bristol-Myers Squibb) and MK-3475 (Pembrolizumab, Merck) were compared in mMLR assays which were performed essentially as described in Example 2. While all antibodies tested were comparable in inducing IFN-γ secretion by CD4+ T cells in minimal MLR assays (FIG. 4A), 0376 showed superior effect in expanding and/or inducing the appearance of cytotoxic Granzyme B+ CD4+ T cells (FIG. 4B).

Figures 5A, 5B:
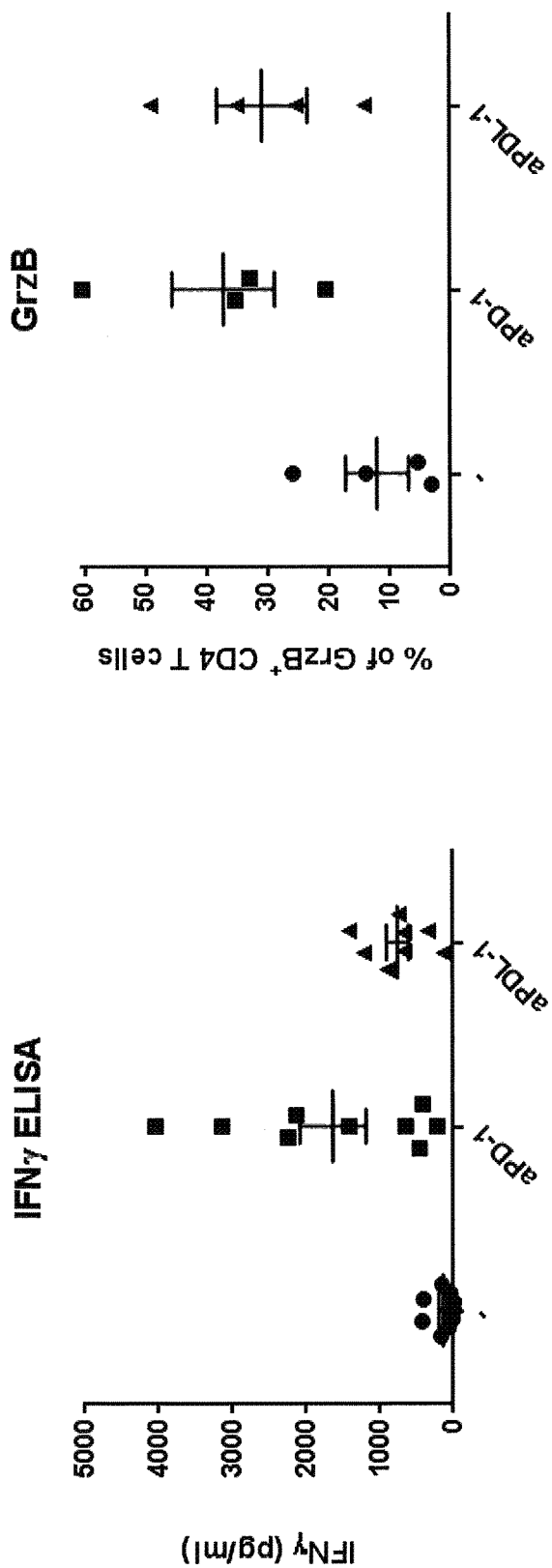
FIG. 5A-B show that anti-PD-L1 treatment induces IFN-γ and Granzyme B production. Levels of IFN-γ present in the supernatant of CD4$^+$ T cells (FIG. 5 A) and expression of Granzyme B by CD4$^+$ T cells (FIG. 5 B) cocultured with allo-DCs with or without anti-PD-1 blocking antibody or anti-PDL-1. Each data point (circle, square or triangle) represents one donor from each independent experiment. In the tested conditions, PD-1 blockade induced more IFN-γ secretion and slightly more Granzyme B expression than PDL-1 blockade.

We also assessed whether blocking the PD-1 ligand, PD-L1, with an anti-PD-L1 antibody (PD-L1 muIgG1 DAPG of Table 5) had a similar effect on CD4+ T cells in minimal MLR assays. All of the anti-PD-1 antibodies (0376, MDX-1106 and MK-3475) and the anti-PD-L1 antibody induced IFN-γ secretion by CD4+ T cells (FIG. 4A, FIG. 5A). The anti-PD-L1 antibody also induced the appearance of cytotoxic Granzyme B+ CD4+ T cells (FIG. 4B and FIG. 5B).

Example 4

CD4+ T Cell Profile in the Peripheral Blood of a Melanoma Patient Treated with Nivolumab Ex-Vivo Phenotypical and Functional Characterization of Melanoma Patient PBMCs After thawing, PBMCs were re-suspended in RPMI 10% FBS at a concentration ranging between $2\times10^5$ and $10^6$ per ml in presence of Golgi Plug (Brefeldin A, BD Bioscience) and Golgi Stop (Monensin, BD Bioscience) and incubated for 12 hours at 37° C. The PBMCs were then washed and surface stained with anti-CD3 (BD Horizon, BD Biosciences), anti-CD8 (BD Biosciences) and anti-CD4 antibodies (BioLegend) followed by permeabilization/fixation with FOXP3/Transcription factor buffer set (eBioscience). The cells were intracellularly stained for FOXP3 (eBioscience), Granzyme B (BD Bioscience), IFN-γ, IL-2 (both from eBioscience) and Ki67 (BD Pharmingen) and acquired at the flow cytometer (LSRFortessa, BD Biosciences).

Cytotoxic CD4+ T cells have been described to exist at very low frequencies in the peripheral blood of healthy individuals and to increase in number during a viral infection where they play a critical role in the anti-viral immune response (Appay, Clin. Exp. Immunol. 138(1):$10^{-13}$ (2004)).

Figure 8:
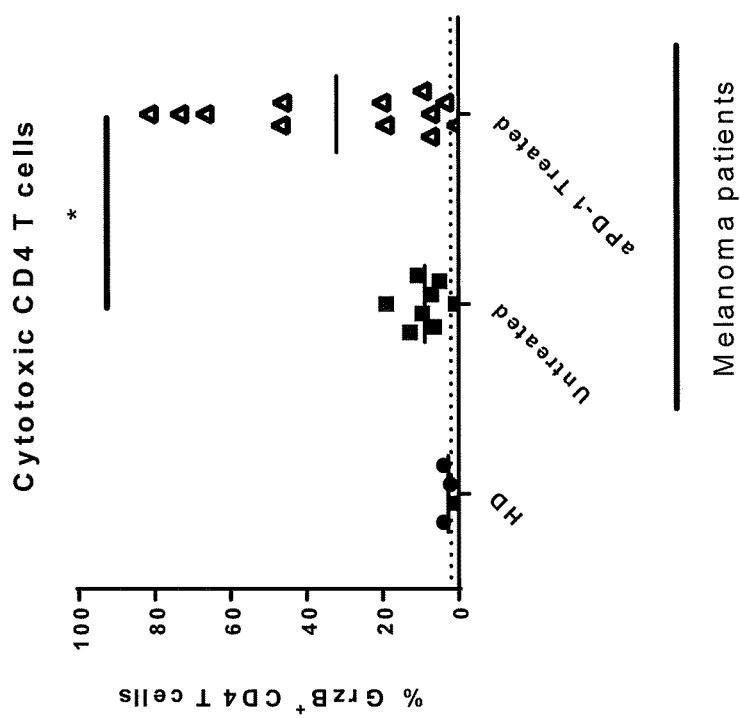
FIG. 8 shows frequencies of cytotoxic CD4$^+$ T cells in healthy donors (HD), untreated- and anti-PD-1 treated-melanoma patients. Each dot represents one donor. This figure shows increased frequencies of cytotoxic CD4$^+$ T cells in the peripheral blood of anti-PD-1 treated melanoma patients (P=0.04).

To confirm our in vitro observations in vivo, we assessed the functional and phenotypical profile of PBMCs from a small cohort of melanoma patients treated or untreated with an anti-PD-1 antibody (MDX-1106) in search of cytotoxic CD4+ T cells (Granzyme B+ CD4+ T cells). After blocking cytokine secretion overnight, we stained the cells with lineage markers and performed intracellular staining for granzyme B. We could significantly (P=0.04) detect the cytotoxic CD4+ T cell population in patients who were treated with the anti-PD-1 antibody (MDX-1106) in PBMCs that were collected at the latest 2 months after the last treatment. This CD4+ cytotoxic T cell population is virtually absent or present only at very low frequencies in healthy donors (FIG. 8).

Figure 6B:
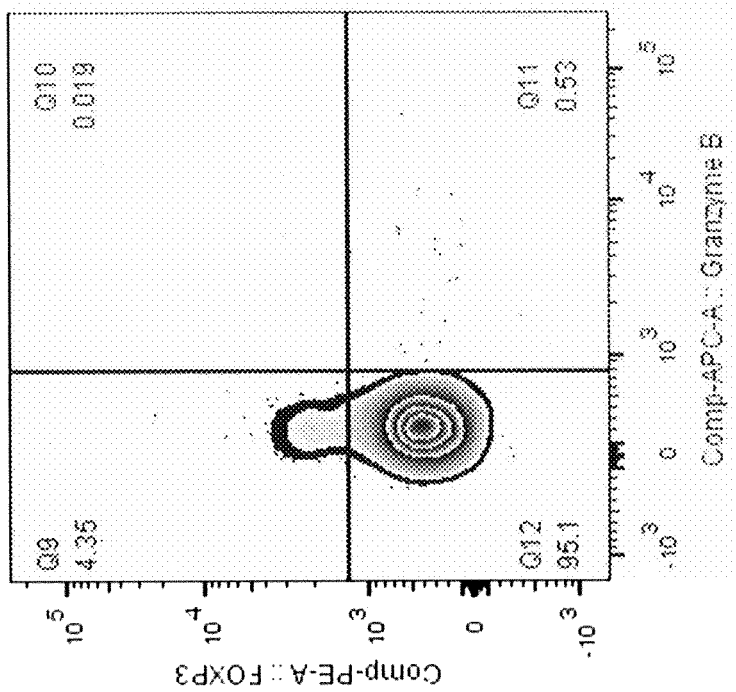
Figure 6A:
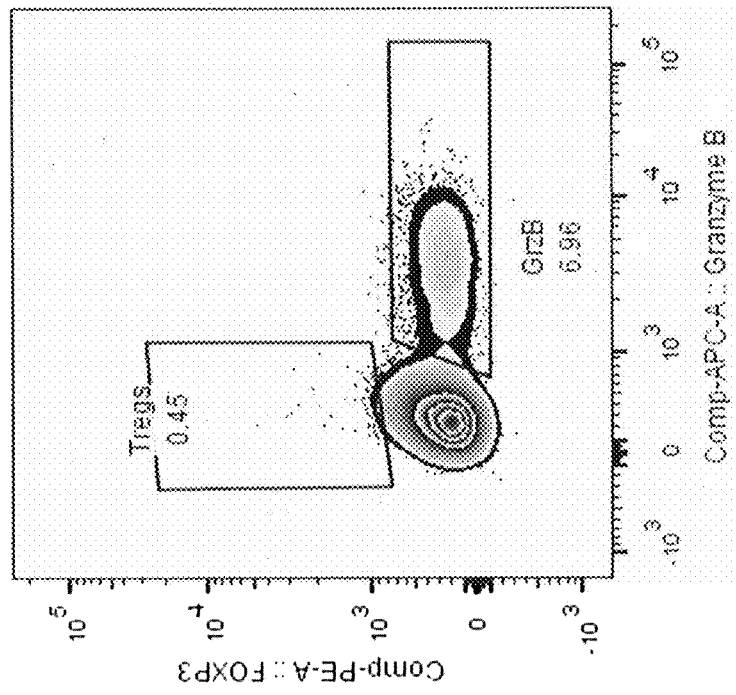
FIGS. 6A and B show CD4$^+$ T cell profile in the peripheral blood of a melanoma patient treated with Nivolumab.

In one particular case we could detect the cytotoxic Granzyme B+ CD4+ T cells in one melanoma patient (HG15443) while he was progression-free but we could not detect the Granzyme B+ CD4+ T cell subpopulation in the same patient at a later time point (HG15952) once the tumor escaped the immune-surveillance (FIGS. 6A and B).

Figure 7:
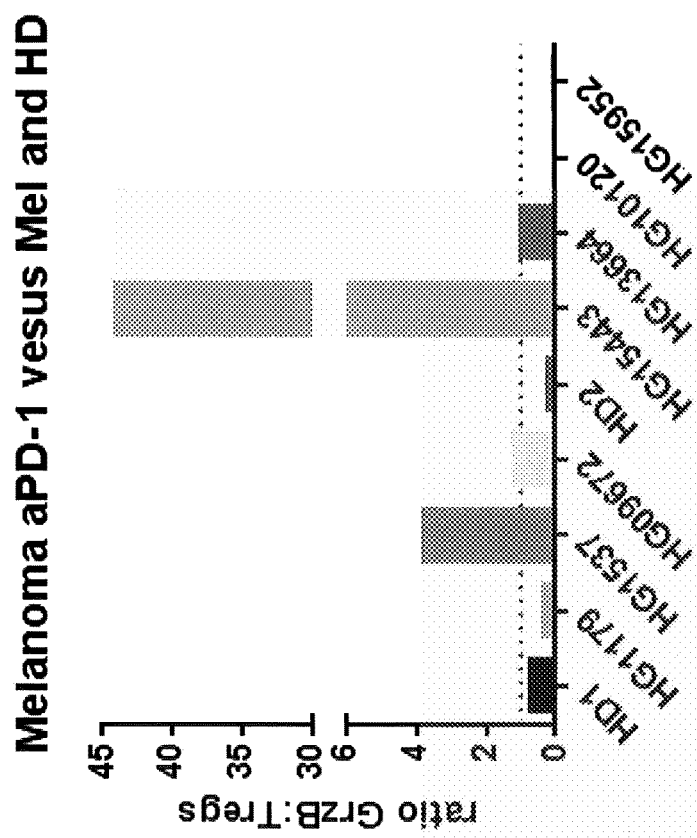
FIG. 7 shows the ratio between Granzyme B$^+$ and Treg cells within the CD4 T cell population in the peripheral blood of melanoma patients treated with Nivolumab. The ratio between Granzyme B$^+$ versus FOXP3$^+$ CD4$^+$ T cells (y axis) highlights two melanoma patients with higher frequencies of cytotoxic CD4$^+$ T cells and reduced Tregs who had a proportionally longer disease free survival period while the other patients had constant deteriorating disease.

We also observed a decrease in regulatory T cell (Tregs, FOXP3+ CD4+ T cells) frequencies in parallel to an increase in the cytotoxic Granzyme B+ CD4+ T cell population in patients treated with the anti-PD-1 antibody (FIG. 6A). Accordingly, we calculated the ratio of cytotoxic CD4+ T cells versus Tregs. We found that two anti-PD-1 antibody treated patients with 3 and 5.6 months disease-free survival had a GranzymeB+:Tregs ratio of 4 and 45, respectively, indicating a positive correlation between a ratio of Granzyme B+ CD4+ T cells and Tregs that is greater than 1 and the clinical benefit of the anti-PD-1 therapy. In contrast, healthy donors and untreated melanoma patients had a GranzymeB:Tregs ratio equal to or below 1 (FIG. 7). Also, the magnitude of the Granzyme B+ CD4+ T cell population relative to the Tregs population seemed to be predictive of durability of response. The patient having a ratio of 4 was observed as disease free for 3 months while the patient that was observed as disease free for 6 months had ratio of 45 (FIG. 7). A larger population size of Granzyme B+ CD4+ T cells, thus, was predictive of longer disease free response.

This is to Applicant's knowledge the first time the mechanism of PD-1 blockage has been elucidated. The findings presented herein have important implications for treatment with PD-1 axis binding molecules, such as anti-PD1 and anti-PD-L1 antibodies. Assessing Granzyme B+ CD4+ T cells can serve as a biomarker to longitudinally monitor a patient's response to the anti-PD-1 therapy. Importantly, the cells can be isolated from peripheral blood rendering it unnecessary to isolate cells or tissue through invasive biopsies. Assessing Granzyme B+ CD4+ T cells, and, more particularly, calculating the GranzymeB:Tregs ratio as described herein can be applied by physicians to monitor rapidly whether a patient is responding to treatment with a PD-1 axis binding molecule, such as an anti-PD-1 or anti-PD-L1 antibody.

Figure 9:
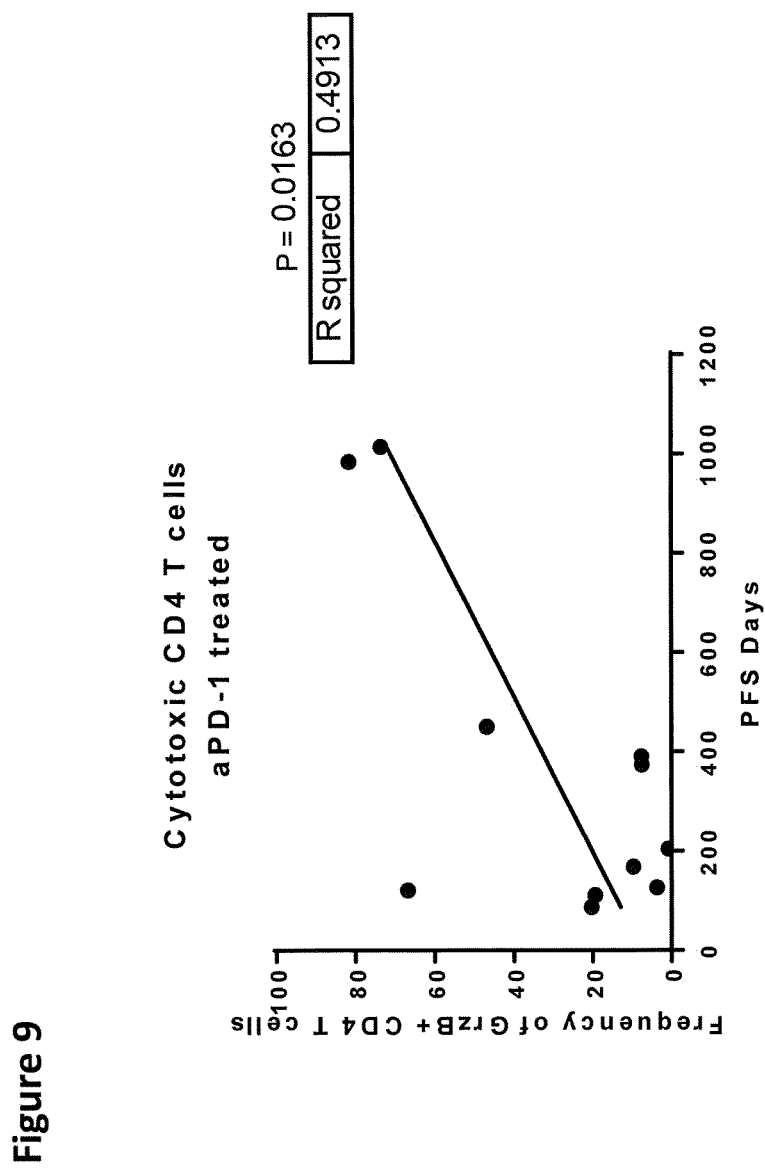
FIG. 9 shows frequencies Granzyme B$^+$ CD4$^+$ T cells from melanoma patients treated with anti-PD-1 therapy versus period in days during which the disease does not progress. Cytotoxic CD4$^+$ T cells frequencies in the peripheral blood correlate with melanoma patient response to the anti-PD1 therapy.

Plotting the frequencies of cytotoxic CD4+ T cells versus the progression free survival (PFS) period revealed a significant correlation (P=0.0163) between the size of the cytotoxic CD4+ T cell population and the period during which the disease is stable or regresses (FIG. 9). This finding indicates a positive correlation between the presence of cytotoxic CD4+ T cells and the clinical benefit of the anti-PD-1 therapy.

Figure 10:
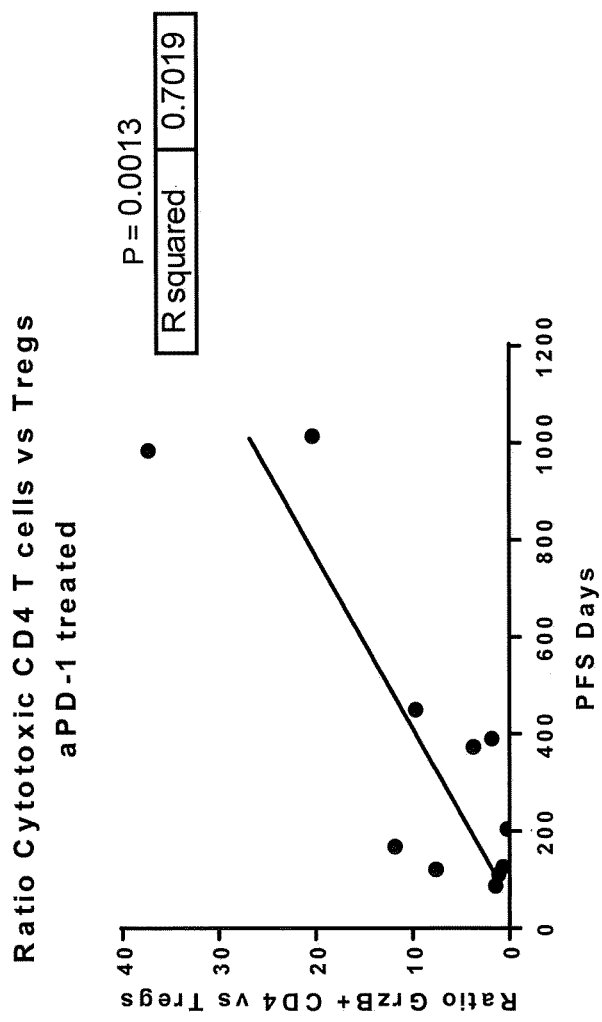
FIG. 10 shows Granzyme B$^+$ CD4$^+$ T cells/Tregs ratio versus progression free period in melanoma patients treated with anti-PD-1 therapy. Ratio between Cytotoxic CD4$^+$ T cell- and Treg-frequencies in the peripheral blood correlate with melanoma patient response to the anti-PD1 therapy.

Unexpectedly, in patients treated with anti-PD-1 antibody we could also observe a decrease in regulatory T cell (Tregs) frequencies in parallel to the increase in cytotoxic CD4+ T cells. We therefore calculated the ratio of cytotoxic CD4+ T cells versus Tregs and depicted it in relation to the disease-free survival period. Interestingly, we found a highly significant correlation between the cytotoxic CD4+ T cells/Tregs ratio and the delayed progression of the disease (P=0.0013) (FIG. 10).

Figure 11:
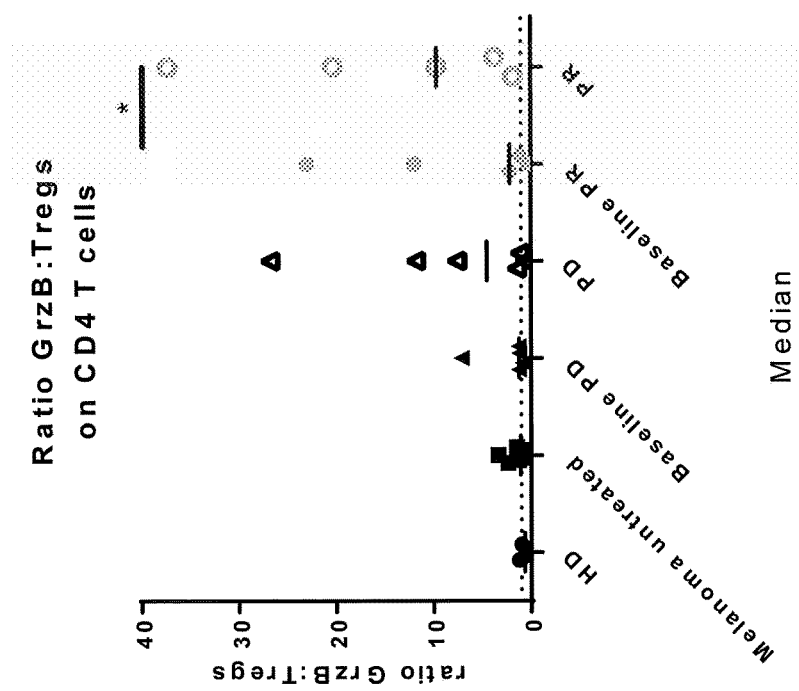
FIG. 11 shows the ratio between Cytotoxic CD4 T$^+$ cell- and Treg-frequencies in the peripheral blood identify anti-PD-1 treated patients and treatment response. Granzyme B$^+$ CD4$^+$ T cells/Tregs ratio is increased in melanoma patients treated with anti-PD-1 antagonist and is even higher in the responder group. Melanoma untreated group depicts patients who did not receive anti-PD-1 while patient prior therapy (baseline group) are divided into PD=progressors and PR=responders based on the clinical outcome. HD indicates healthy donors. Each dots represents one donor.

Patient stratification based on the treatment and response to the treatment revealed that anti-PD-1 therapy induces a significant increase (P=0.02), for the responder group, in cytotoxic CD4+ T cells versus Tregs when compared to a time point prior treatment, indicated as baseline. In addition there is a clear tendency in an increase of cytotoxic CD4+ T cells to Tregs detriment in those patients responding to the anti-PD-1 therapy versus those patients with progressive disease (FIG. 11).

This finding not only sheds light on the underpinning mechanism of PD-1 blockade but provides a useful biomarker to longitudinally monitor the patient-response to the anti-PD-1 therapy by simply collect a small amount of peripheral blood. This tool would eventually allow medical doctors to follow and estimate in a timely fashion whether the patient is responding to anti-PD-1 treatment and opt for ad-hoc combination strategy to increase the patient chances to mount an effective tumor-specific immune response.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for treating a human individual suffering from a cancer comprising first administering a treatment comprising an effective amount of a PD-1 axis binding antagonist to the individual, wherein the PD-1 axis binding antagonist is an antibody; determining whether or not the individual is responding to the treatment; and either continuing or discontinuing the treatment, wherein
the determining step comprises obtaining a ratio between Granzyme $B^+$ $CD4^+$ T cells and $FOXP3^+$ $CD4^+$ T cells (Tregs) found in a peripheral blood mononuclear cell (PBMC) sample obtained from the peripheral blood of the individual, wherein
if the ratio is 1 or greater, determining that the individual is responding to the treatment and continuing administration of the treatment to the individual; and
if the ratio is less than 1, determining that the individual is not responding to the treatment and discontinuing administration of the treatment to the individual.

2. The method of claim 1, wherein the cancer is melanoma.

3. The method of claim 1, wherein the PD-1 axis binding antagonist is a PD-1 binding antagonist.

4. The method of claim 3, wherein the PD-1 binding antagonist inhibits the binding of PD-1 to PD-L1.

5. The method of claim 4, wherein the PD-1 binding antagonist inhibits the binding of PD-1 to both PD-L1 and PD-L2.

6. The method of claim 1, wherein the antibody is MDX-1106 (nivolumab).

* * * * *

SEQUENCE LISTING

```
<160> NUMBER OF SEQ ID NOS: 43

<210> SEQ ID NO 1
<211> LENGTH: 440
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
```

```
                   50                  55                  60
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                     85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 2
<211> LENGTH: 214
<212> TYPE: PRT
<213> ORGANISM: Artificial Sequence
```

<220> FEATURE:
<223> OTHER INFORMATION: Synthetic Construct

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 118
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala

```
                 115

<210> SEQ ID NO 4
<211> LENGTH: 108
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (6)..(6)
<223> OTHER INFORMATION: Xaa is D or G

<400> SEQUENCE: 5

Gly Phe Thr Phe Ser Xaa Ser Trp Ile His
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (4)..(4)
<223> OTHER INFORMATION: Xaa is S or L
<220> FEATURE:
<221> NAME/KEY: Xaa
<222> LOCATION: (10)..(10)
<223> OTHER INFORMATION: Xaa is T or S

<400> SEQUENCE: 6

Ala Trp Ile Xaa Pro Tyr Gly Gly Ser Xaa Tyr Tyr Ala Asp Ser Val
1               5                   10                  15

Lys Gly

<210> SEQ ID NO 7
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 7

Arg His Trp Pro Gly Gly Phe Asp Tyr
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 9
<211> LENGTH: 13
<212> TYPE: PRT
<213> ORGANISM: Artificial Sequence
<220> FEATURE:
<223> OTHER INFORMATION: Synthetic Construct

<400> SEQUENCE: 9

Trp Val Arg Gln Ala Pro Gly Lys Gly Leu Glu Trp Val
1               5                   10

<210> SEQ ID NO 10
<211> LENGTH: 32
<212> TYPE: PRT
<213> ORGANISM: Artificial Sequence
<220> FEATURE:
<223> OTHER INFORMATION: Synthetic Construct

<400> SEQUENCE: 10

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Trp Gly Gln Gly Thr Leu Val Thr Val Ser Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (5)..(5)
<223> OTHER INFORMATION: Xaa is D or V
<220> FEATURE:
<221> NAME/KEY: Xaa
<222> LOCATION: (6)..(6)

```
<223> OTHER INFORMATION: Xaa is V or I
<220> FEATURE:
<221> NAME/KEY: Xaa
<222> LOCATION: (7)..(7)
<223> OTHER INFORMATION: Xaa is S or N
<220> FEATURE:
<221> NAME/KEY: Xaa
<222> LOCATION: (9)..(9)
<223> OTHER INFORMATION: Xaa is A or F
<220> FEATURE:
<221> NAME/KEY: Xaa
<222> LOCATION: (10)..(10)
<223> OTHER INFORMATION: Xaa is V or L

<400> SEQUENCE: 12

Arg Ala Ser Gln Xaa Xaa Xaa Thr Xaa Xaa Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (4)..(4)
<223> OTHER INFORMATION: Xaa is F or T
<220> FEATURE:
<221> NAME/KEY: Xaa
<222> LOCATION: (6)..(6)
<223> OTHER INFORMATION: Xaa is Y or A

<400> SEQUENCE: 13

Ser Ala Ser Xaa Leu Xaa Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: Xaa
<222> LOCATION: (3)..(3)
<223> OTHER INFORMATION: Xaa is Y, G, F, or S
<220> FEATURE:
<221> NAME/KEY: Xaa
<222> LOCATION: (4)..(4)
<223> OTHER INFORMATION: Xaa is L, Y, F, or W
<220> FEATURE:
<221> NAME/KEY: Xaa
<222> LOCATION: (5)..(5)
<223> OTHER INFORMATION: Xaa is Y, N, A, T, G, F, or I
<220> FEATURE:
<221> NAME/KEY: Xaa
<222> LOCATION: (6)..(6)
<223> OTHER INFORMATION: Xaa is H, V, P, T, or I
<220> FEATURE:
<221> NAME/KEY: Xaa
<222> LOCATION: (8)..(8)
<223> OTHER INFORMATION: Xaa is A, W, R, P, or T

<400> SEQUENCE: 14

Gln Gln Xaa Xaa Xaa Xaa Pro Xaa Thr
1               5

<210> SEQ ID NO 15
<211> LENGTH: 23
<212> TYPE: PRT
<213> ORGANISM: Artificial Sequence
<220> FEATURE:
```

<223> OTHER INFORMATION: Synthetic Construct

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic Construct

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Phe Gly Gln Gly Thr Lys Val Glu Ile Lys Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Gly Phe Thr Phe Ser Asp Ser Trp Ile His
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Ala Trp Ile Ser Pro Tyr Gly Gly Ser Thr Tyr Tyr Ala Asp Ser Val
1               5                   10                  15

Lys Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Arg His Trp Pro Gly Gly Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Arg Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Ser Ala Ser Phe Leu Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gln Gln Tyr Leu Tyr His Pro Ala Thr
1               5

<210> SEQ ID NO 25
<211> LENGTH: 118
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                    85                  90                  95
Ala Arg Arg His Trp Pro Gly Gly Phe Asp Tyr Trp Gly Gln Gly Thr
            100                 105                 110

Leu Val Thr Val Ser Ser
        115

<210> SEQ ID NO 26
<211> LENGTH: 122
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Trp Gly Gln Gly Thr Leu Val Thr Val Ser Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Phe Gly Gln Gly Thr Lys Val Glu Ile Lys
1               5                   10

<210> SEQ ID NO 29
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Val Glu Ser Gly Gly Gly Leu Val Gln Pro Gly Gly
```

Ser Leu Arg Leu Ser Cys Ala Ala Ser Gly Phe Thr Phe Ser
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Trp Val Arg Gln Ala Pro Gly Lys Gly Leu Glu Trp Val Ala
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Synthetic Construct

<400> SEQUENCE: 31

Trp Gly Gln Gly Thr Leu Val Thr Val Ser Ser Ala Ser Thr Lys
1               5                   10                  15

<210> SEQ ID NO 32
<211> LENGTH: 447
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 33
<211> LENGTH: 214
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 7
<212> TYPE: PRT
<213> ORGANISM: Artificial Sequence
<220> FEATURE:
<223> OTHER INFORMATION: 0376 HVR-H1

<400> SEQUENCE: 34

Gly Phe Ser Phe Ser Ser Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: 0376 HVR-H2

<400> SEQUENCE: 35

Gly Gly Arg
1

<210> SEQ ID NO 36
<211> LENGTH: 9
<212> TYPE: PRT
<213> ORGANISM: Artificial Sequence
<220> FEATURE:
<223> OTHER INFORMATION: 0376 HVR-H3

<400> SEQUENCE: 36

Thr Gly Arg Val Tyr Phe Ala Leu Asp
1               5

<210> SEQ ID NO 37
<211> LENGTH: 11
<212> TYPE: PRT
<213> ORGANISM: Artificial Sequence
<220> FEATURE:
<223> OTHER INFORMATION: 0376 HVR-L1

<400> SEQUENCE: 37

Ser Glu Ser Val Asp Thr Ser Asp Asn Ser Phe
1               5                   10

<210> SEQ ID NO 38
<211> LENGTH: 3
<212> TYPE: PRT
<213> ORGANISM: Artificial Sequence
<220> FEATURE:
<223> OTHER INFORMATION: 0376 HVR-L2
```

```
<400> SEQUENCE: 38

Arg Ser Ser
1

<210> SEQ ID NO 39
<211> LENGTH: 6
<212> TYPE: PRT
<213> ORGANISM: Artificial Sequence
<220> FEATURE:
<223> OTHER INFORMATION: 0376 HVR-L3

<400> SEQUENCE: 39

Asn Tyr Asp Val Pro Trp
1               5

<210> SEQ ID NO 40
<211> LENGTH: 120
<212> TYPE: PRT
<213> ORGANISM: Artificial Sequence
<220> FEATURE:
<223> OTHER INFORMATION: 0376 VH

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser
        115                 120

<210> SEQ ID NO 41
<211> LENGTH: 111
<212> TYPE: PRT
<213> ORGANISM: Artificial Sequence
<220> FEATURE:
<223> OTHER INFORMATION: 0376 VL

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95
```

```
Asp Val Pro Trp Thr Phe Gly Gln Gly Thr Lys Val Glu Ile Lys
                100                 105                 110

<210> SEQ ID NO 42
<211> LENGTH: 442
<212> TYPE: PRT
<213> ORGANISM: Artificial Sequence
<220> FEATURE:
<223> OTHER INFORMATION: aPDL1 HC

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Gln Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Ala Ile Ser Lys Asp Asp Pro Glu Val Gln Phe Ser Trp
            260                 265                 270

Phe Val Asp Asp Val Glu Val His Thr Ala Gln Thr Lys Pro Arg Glu
        275                 280                 285

Glu Gln Ile Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Gly Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350
```

```
Met Ala Lys Asp Lys Val Ser Leu Thr Cys Met Ile Thr Asn Phe Phe
        355                 360                 365

Pro Glu Asp Ile Thr Val Glu Trp Gln Trp Asn Gly Gln Pro Ala Glu
        370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
        435                 440

<210> SEQ ID NO 43
<211> LENGTH: 214
<212> TYPE: PRT
<213> ORGANISM: Artificial Sequence
<220> FEATURE:
<223> OTHER INFORMATION: aPDL1 LC

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```